US011452554B2

(12) United States Patent
Patel et al.

(10) Patent No.: US 11,452,554 B2
(45) Date of Patent: Sep. 27, 2022

(54) SYSTEM AND METHOD FOR FASTENING OF TWO OR MORE INTERACTING ELEMENTS

(71) Applicant: The Regents of the University of Colorado, Denver, CO (US)

(72) Inventors: Vikas Patel, Denver, CO (US); Jay Nanninga, Monrovia, MD (US)

(73) Assignee: The Regents of the University of Colorado, Denver, CO (US)

(*) Notice: Subject to any disclaimer, the term of this patent is extended or adjusted under 35 U.S.C. 154(b) by 359 days.

(21) Appl. No.: 16/654,691

(22) Filed: Oct. 16, 2019

(65) Prior Publication Data

US 2020/0054373 A1 Feb. 20, 2020

Related U.S. Application Data

(63) Continuation-in-part of application No. 15/325,822, filed as application No. PCT/US2015/040729 on Jul. 16, 2015, now Pat. No. 10,786,289.

(60) Provisional application No. 62/025,163, filed on Jul. 16, 2014.

(51) Int. Cl.
*A61B 17/80* (2006.01)

(52) U.S. Cl.
CPC ................ *A61B 17/8057* (2013.01)

(58) Field of Classification Search
CPC ............ A61B 17/8057; A61B 17/8052; A61B 17/8033; A61B 17/8019; A61F 2/44–447; A61F 2002/4415–4495

USPC .......................................... 606/273, 280–321
See application file for complete search history.

(56) References Cited

U.S. PATENT DOCUMENTS

| | | | |
|---|---|---|---|
| 5,954,722 A * | 9/1999 | Bono | A61B 17/863 606/281 |
| 6,432,106 B1 * | 8/2002 | Fraser | A61F 2/30771 623/17.11 |
| 6,764,489 B2 * | 7/2004 | Ferree | A61B 17/7059 606/279 |
| 7,175,625 B2 * | 2/2007 | Culbert | A61F 2/0811 606/326 |
| 7,887,595 B1 * | 2/2011 | Pimenta | A61F 2/447 623/17.16 |
| 7,914,562 B2 * | 3/2011 | Zielinski | A61B 17/8866 606/915 |

(Continued)

*Primary Examiner* — Matthew J Lawson
(74) *Attorney, Agent, or Firm* — Nicholas Pfeifer; Smith & Hopen, P. A.

(57) ABSTRACT

A method for securing a first interacting element to a second interacting element is provided. The first interacting element includes a lateral surface established by a first surface and a second surface and at least a portion of the lateral surface includes a thread receipt. The second interacting element includes a distal end and a proximal end that establishes a body therebetween. The body has a thread that is configured to at least partially engage with the thread receipt of the first interacting element. The second interacting element is then inserted at least partially through the surface of an object. The thread receipt of the first interacting element is then abutted adjacent to the thread of the second interacting element. Upon rotation of the second interacting element the thread of the second interacting element at least partially engaged with the thread receipt of the fist interacting element.

20 Claims, 31 Drawing Sheets

(56) References Cited

U.S. PATENT DOCUMENTS

| | | | | |
|---|---|---|---|---|
| 8,690,918 B1* | 4/2014 | Williams | ............ | A61B 17/7068 606/280 |
| 8,715,284 B2* | 5/2014 | Culbert | ................ | A61B 17/742 606/65 |
| 8,740,955 B2* | 6/2014 | Bottlang | .............. | A61B 17/863 606/310 |
| 8,932,358 B1* | 1/2015 | Nehls | .................... | A61F 2/4455 623/17.16 |
| 8,951,588 B2* | 2/2015 | Block | .................... | A23G 3/563 426/104 |
| 9,220,609 B2* | 12/2015 | Mueller | ................ | A61B 17/864 |
| 9,522,028 B2* | 12/2016 | Warren | ................ | A61B 17/864 |
| 10,213,237 B2* | 2/2019 | Wiederkehr | ........ | A61B 17/8014 |
| 2003/0187441 A1* | 10/2003 | Bolger | .................... | A61F 2/447 606/295 |
| 2008/0161925 A1* | 7/2008 | Brittan | .................. | A61F 2/4465 623/17.16 |
| 2008/0300637 A1* | 12/2008 | Austin | ............... | A61B 17/8033 606/290 |
| 2008/0312742 A1* | 12/2008 | Abernathie | ............. | A61F 2/447 623/17.16 |
| 2010/0094357 A1* | 4/2010 | Wallenstein | ....... | A61B 17/8685 606/291 |
| 2010/0274358 A1* | 10/2010 | Mueller | ............. | A61B 17/7059 623/17.16 |
| 2011/0004253 A1* | 1/2011 | Fraser | .................... | A61F 2/4455 606/281 |
| 2011/0118742 A1* | 5/2011 | Hulliger | ............. | A61B 17/8047 606/70 |
| 2011/0270320 A1* | 11/2011 | Oh | .................... | A61B 17/8047 606/290 |

\* cited by examiner

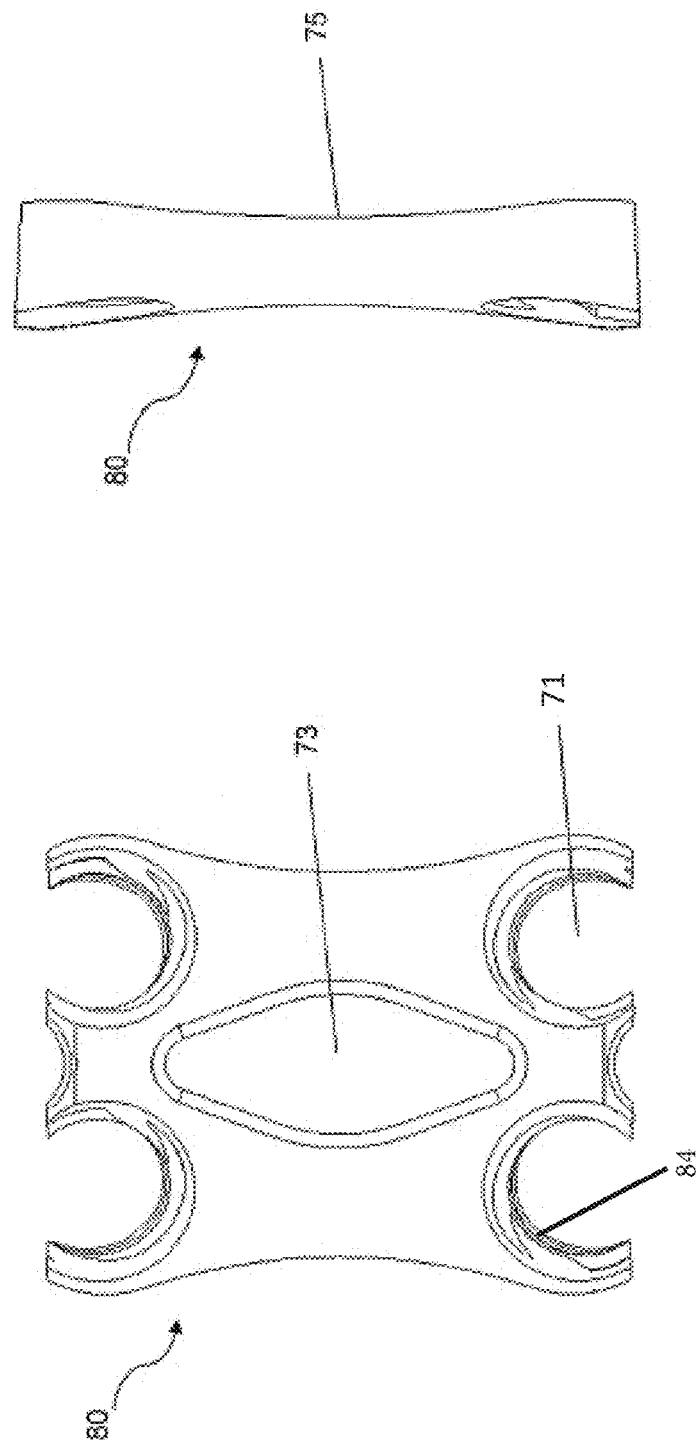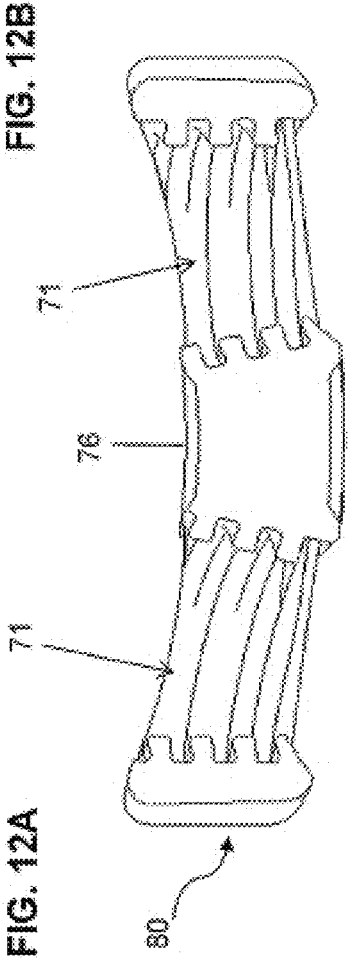
FIG. 12A
FIG. 12B
FIG. 12C

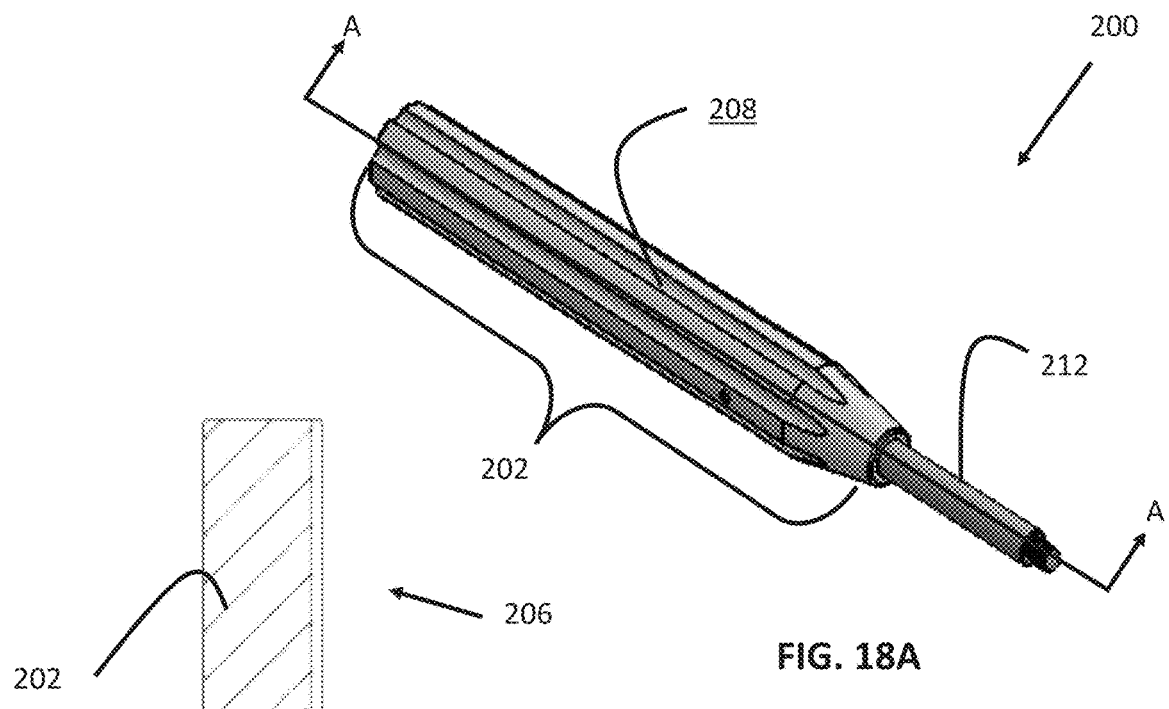
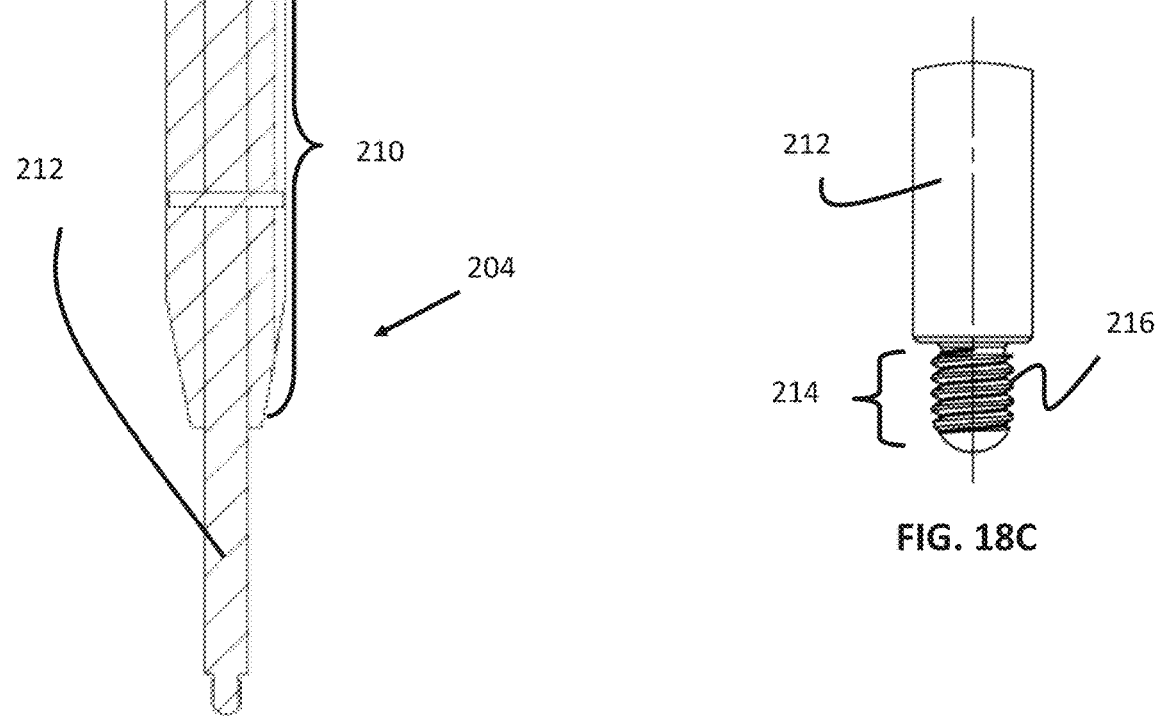
FIG. 18A
FIG. 18B
FIG. 18C

SYSTEM AND METHOD FOR FASTENING OF TWO OR MORE INTERACTING ELEMENTS

CROSS-REFERENCE TO RELATED APPLICATIONS

This nonprovisional application is a continuation-in-part ("CIP") of and claims priority to Non-provisional application Ser. No. 15/325,822, entitled "SYSTEM AND METHODS FOR POSITIONING OF TWO OR MORE INTERACTING ELEMENTS," filed Jan. 12, 2017, which claims priority to the PCT Application No. PCT/US15/40729, entitled "SYSTEM AND METHODS FOR POSITIONING OF TWO OR MORE INTERACTING ELEMENTS", filed Jul. 16, 2015, which claims priority to U.S. Provisional Patent Application 62/025,163, entitled "SYSTEM AND METHODS FOR POSITIONING OF TWO OR MORE INTERACTING ELEMENTS," filed Jul. 16, 2014.

BACKGROUND OF THE INVENTION

1. Field of the Invention

The present invention relates generally to systems and methods for implantable orthopedic devices. More specifically, the present invention pertains to the partial placement of one or more fasteners prior to securing a plate to a vertebral column.

2. Brief Description of the Prior Art

From time to time, a consumer may be motivated to position two or more interacting elements such that they are configured to maintain a particular position for a considerable period of time, such as a few minutes, a few hours, a few days, or a few weeks. As an example, if a human or animal breaks or fractures a bone, the treatment may include positioning one or more interacting elements relative to the bone to stabilize the bone in an optimized position for healing.

One or more interacting elements may include, for example, a plate and one or more fastener elements for attachment to vertebrae in order to immobilize, stabilize and/or align those vertebrae. The plate may be used for a variety of conditions including, for example, providing added strength and rigidity after fusion of adjacent vertebrae, securing vertebrae together where an intervening vertebrae has been removed and replaced, correcting spinal deformities, and correcting instability caused by trauma, fractures, tumors, advanced degenerative discs, infection, or congenital or acquired deformities.

Plates used for these types of conditions generally span the distance between two, three, four, or more vertebrae, as required in a given situation. The plate generally curves so as to fit the curvature of the vertebrae to which they are attached. Additionally, a plate of this type generally matches the curvature of the cervical spine. A plate of this type is typically provided with holes for fastener elements known as "bone screws." Pilot holes are drilled into the adjacent vertebrae by instruments that are known in the art, such as surgical drills, after which the plate is attached by the bone screws which pass through the pilot holes in the plate for securing the plate to the adjacent vertebrae.

While certain systems for stabilizing a bone exist, such known systems are associated with certain disadvantages. Thus, there is a demand for improved systems and methods for positioning two or more interacting elements relative to one another such as a plate and one or more fastener elements, for use in applications such as stabilizing fractures and cervical fixation to name a few. The present invention satisfies this demand.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

For purposes of this application, the present invention is discussed in reference to one or more interacting elements configured to stabilize the position of an object in the form of a plate and one or more fastener elements, but the discussion is merely exemplary. The present invention is applicable to any system in which two or more interacting elements are configured to maintain a particular configuration and/or position.

Certain embodiments of the system and method of the present invention include a fastener element with a body component and a thread component. Other embodiments of a fastener element may include multiple body components, each of which may include a respective thread component. Certain embodiments of a thread component may be configured to maximize the amount of weight the connection between the two interacting components can bear. Other embodiments may be configured to maximize the flexibility of the connection between the two interacting components.

One object of certain embodiments of the present invention is that it permits inserting a second interacting element, such as a fastener element, into a first interacting element, such as a plate, so that the first surface of the second interacting element is flush with or remains below the first surface of a first interacting element.

Another object of certain embodiments of the present invention is that it facilitates a removable connection between a first interacting element and a second interacting element, wherein the second interacting element is connected along the lateral surface of the first interacting element; for example, a fastener element connected along the lateral edge of the plate.

Advantageously, in embodiments in which the first interacting element is a plate for setting bones, such embodiments permit positioning the plate close to a joint without impinging the adjacent bone in the joint. Another advantage of such embodiments is that it may use smaller plates for setting bones relative to other connection methods while maintaining the strength of the connection. Alternatively, the connection may be a stronger and more rigid interface between the first interacting element and the second interacting element relative to other connection methods.

Another object of certain embodiments of the present invention is to include different thread components on the body component of the fastener element defining a first body component and a second body component. The first body component comprises a first thread component that wraps around a first portion of the body component of the fastener element and a second body component comprises a second thread component wrapped around a second portion of the body component.

An embodiment of the present invention is a method for securing a first interacting element to a second interacting element. The first interacting element has first surface and second surface and a thickness therebetween establishing a lateral surface. At least a portion of the lateral surface includes a thread receipt. Second interacting element includes a distal end and a proximal end that establishes a body therebetween. The body has a thread at least partially disposed around a surface of the body and is configured to at least partially engage the thread receipt on the first interacting element. The second interacting element is at least partially inserted through a surface of an object. Furthermore, the thread receipt of the first interacting element is positioned adjacent to the thread of the second interacting element and the second interacting element is rotated such that the thread of the second interacting element at least partially engages the thread receipt of the first interacting element.

In an embodiment, the second interacting element has a first thread at least partially disposed around a first portion of a surface of the body and a second thread at least partially disposed around a second portion of the surface of the body. The first thread is configured to at least partially engage the thread receipt on the first interacting element and the second thread is configured to propel the second interacting element through a surface of an object when the second interacting element is rotated. The second interacting element is partially threaded through the surface of the object. Then, the thread receipt of the first interacting element is positioned adjacent to the first thread of the second interacting element and the second interacting element is rotated such that the first thread of the second interacting element engages the thread receipt of the first interacting element.

An embodiment of the present invention further includes the first interacting element having a viewing aperture disposed therethrough from the first surface to the second surface.

An embodiment of the present invention further includes an end cap positioned at the proximal end of the body of the second interacting element. The end cap is relatively wider than the body of the second interacting element and thus prevents the second interacting element from being rotated further into the first interacting element when the end cap contacts the first interacting element.

An embodiment of the present invention includes drilling a pilot hole in the object to guide the insertion of the second interacting element into the object. An embodiment of the second interacting may include a cutting flute configured to facilitate a self-tapping capability.

An embodiment of the present invention includes the first interacting element having an engagement aperture that is at least partially disposed through the first or second surface. The engagement aperture includes an internal thread. A handle is configured to be removably coupled to the internal thread of the engagement aperture of the first interacting element thereby increasing control over the placement of the first interacting element.

In an embodiment, the size of the thread of the second interacting element is static throughout the entire thread.

In an embodiment, the thread includes a thread base surface and an outer thread surface, where the outer thread surface is smaller in length near a thread termination end and larger in length near a thread origination end, such that the thread is configured to permit locking of the thread within the thread receipt.

It is contemplated that a thread component according to the invention may be of a generally helical shape with the same or varying pitch along the length of the body component. For purposes of this application, the pitch of a helix is the width of one complete helix turn, measured parallel to the axis of the helix.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which:

FIG. 12A illustrates a top view of a first interacting element in the form of a plate.

FIG. 12B illustrates a side view of a first interacting element.

FIG. 12C illustrates a cross-section view of an embodiment of a first interacting element.

FIG. 18A illustrates a perspective view of a handle.

FIG. 18B illustrates a cross-sectional view of a handle taken along line A-A in FIG. 18A.

FIG. 18C illustrates an engagement portion of a handle.

DETAILED DESCRIPTION OF THE INVENTION

For convenience of description, terms such as "above," "below," "upper," "lower," "outer," "inner," "bottom," and "top" are used in this application to refer to the system and the components of the system in an orientation illustrated in the accompanying drawings. However, it will be understood that the embodiments of the invention described in this application advantageously can be used in a variety of orientations.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

Figure 1:
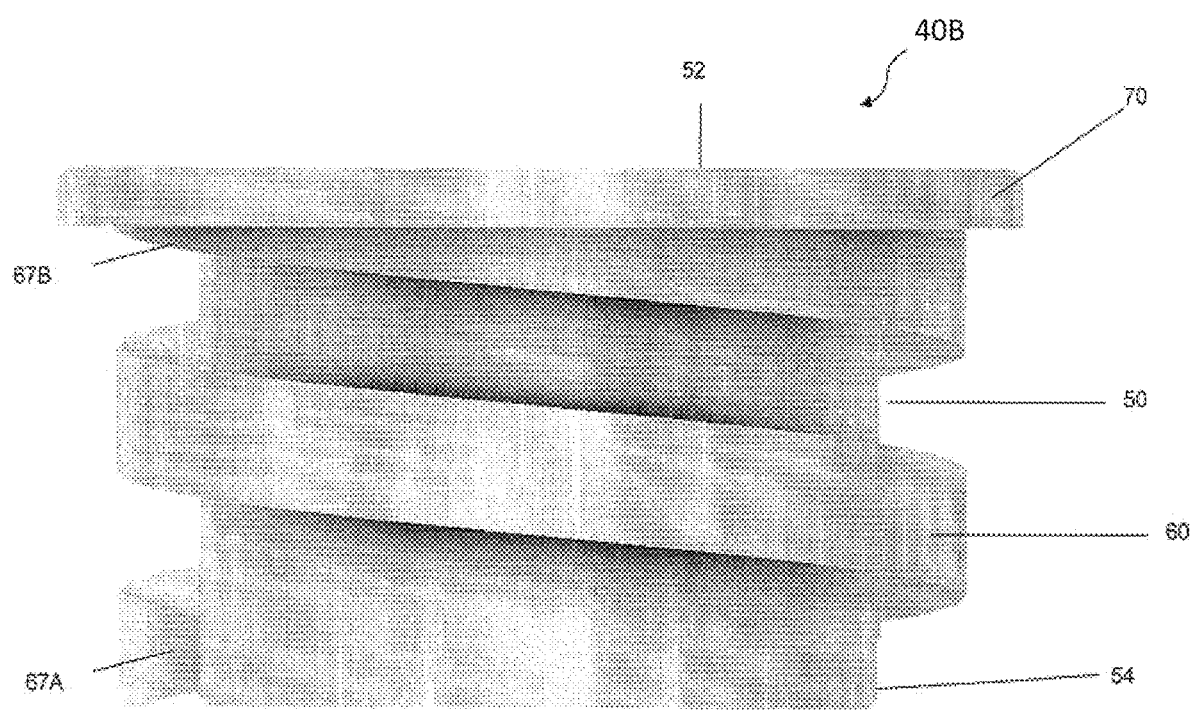
FIG. 1 illustrates an embodiment of a second interacting element including a body component and a thread component.

Certain embodiments of assembly 10 and methods of the present invention include first interacting element 40A and second interacting element 40B. As illustrated in FIG. 1, embodiments of second interacting element 40B may be in the form of fastener 70 and include body component 50 and thread component 60. Body component 50 may include end cap 52 and core body 54. Core body 54 may be configured as the foundation on which thread component 60 is positioned or formed adjacent to thread component 60.

Figure 5:
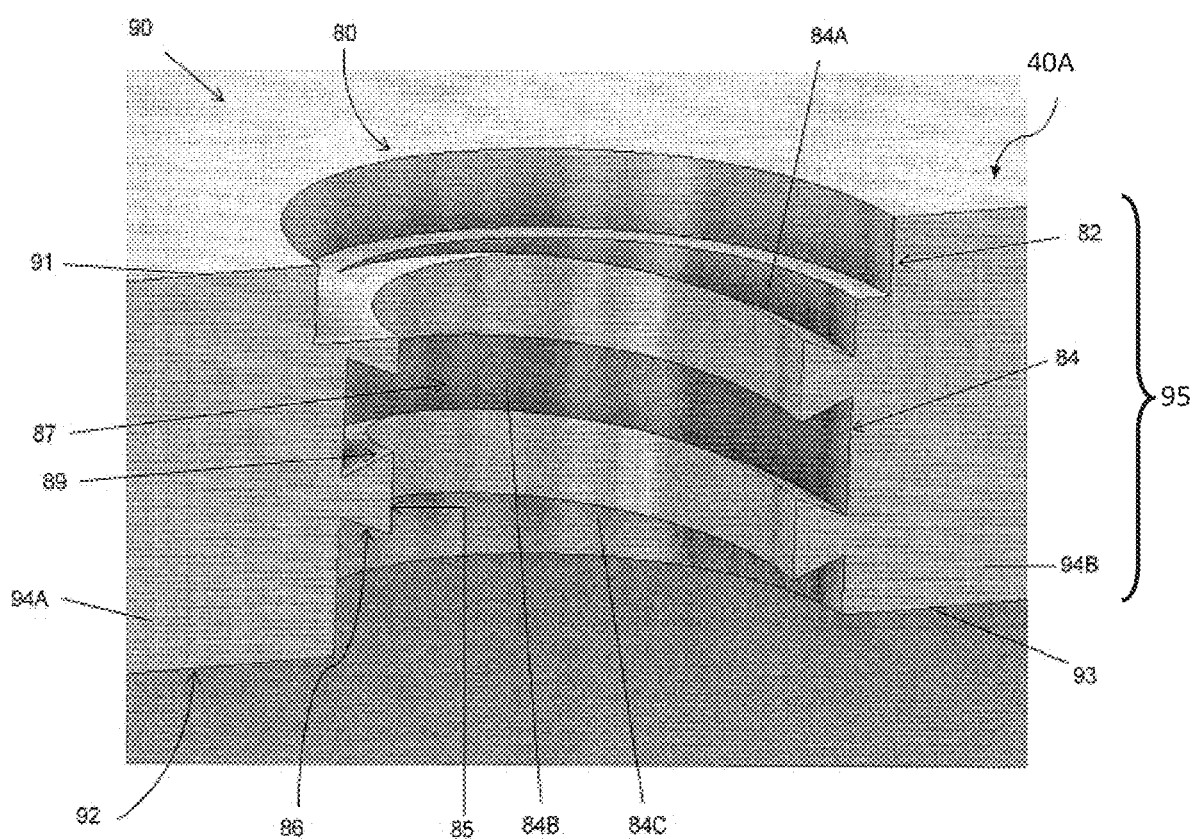
FIG. 5 illustrates an embodiment of a first interacting element, in the form of a plate.

End cap 52 may be configured to be relatively wider than core body 54, such that end cap 52 effectively forms the end of thread component 60, such that fastener 70 cannot be rotated any further when end cap 52 meets with end cap receiving element 82 in plate 80 (see e.g., FIG. 5). Other embodiments may include no end cap 52 or end cap 52 that has the same or smaller cross-sectional diameter than core body 54. Thread component 60 may include thread termination end 67A and thread origination end 67B. Thread component 60 is positioned relative to body component 50, such that upon rotating second interacting element 40B, thread component 60 is received by thread receiving element 84 of first interacting element 40A (see e.g., FIG. 5).

Figure 2:
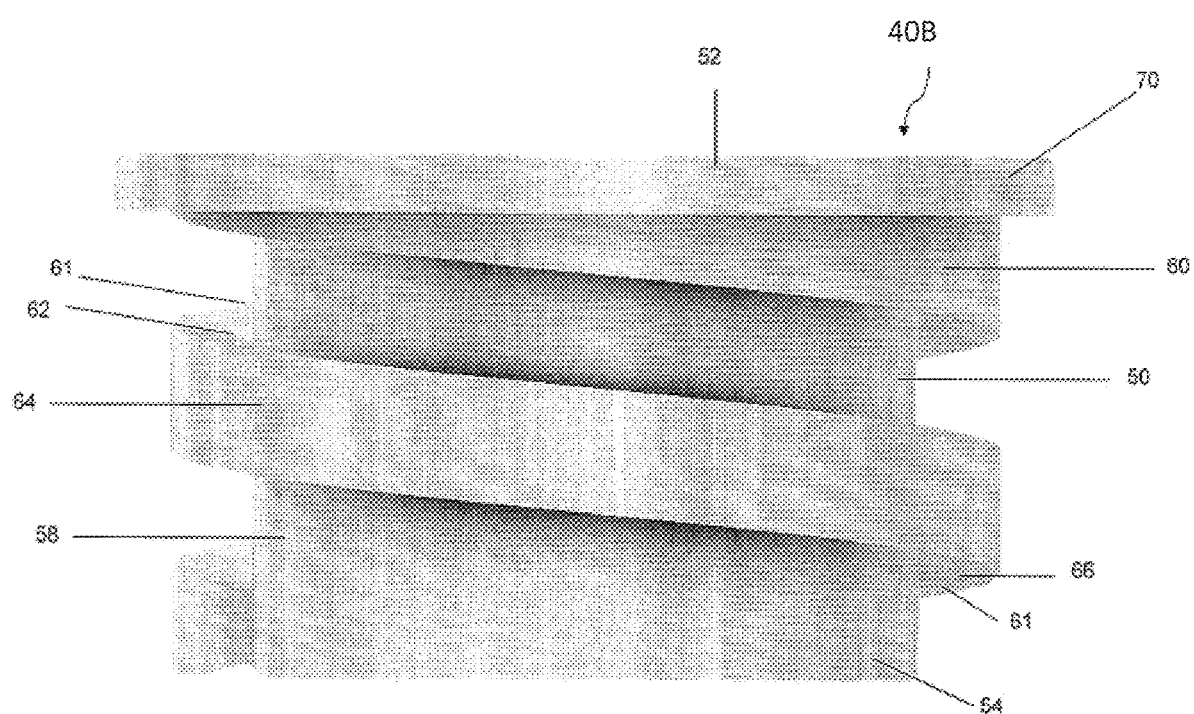
FIG. 2 illustrates additional features of a second interacting element including a body component and a thread component.

As illustrated in FIG. 2, thread component 60 may include outer thread surface 64 that may be generally parallel to outer core body surface 58 of core body 54. In addition, thread component 60 may include two or more side thread surfaces 61 configured to adjoin outer thread surface 64 to outer core body surface 58. The embodiment illustrated in FIG. 2 includes upper thread surface 62 and lower thread surface 66.

In certain embodiments, the entire second interacting element 40B is a single unit formed by, for example, injection molding. In other embodiments, certain portions of second interacting element 40B are formed separately from thread component 60 and then the pieces are subsequently attached together.

Figure 3A:
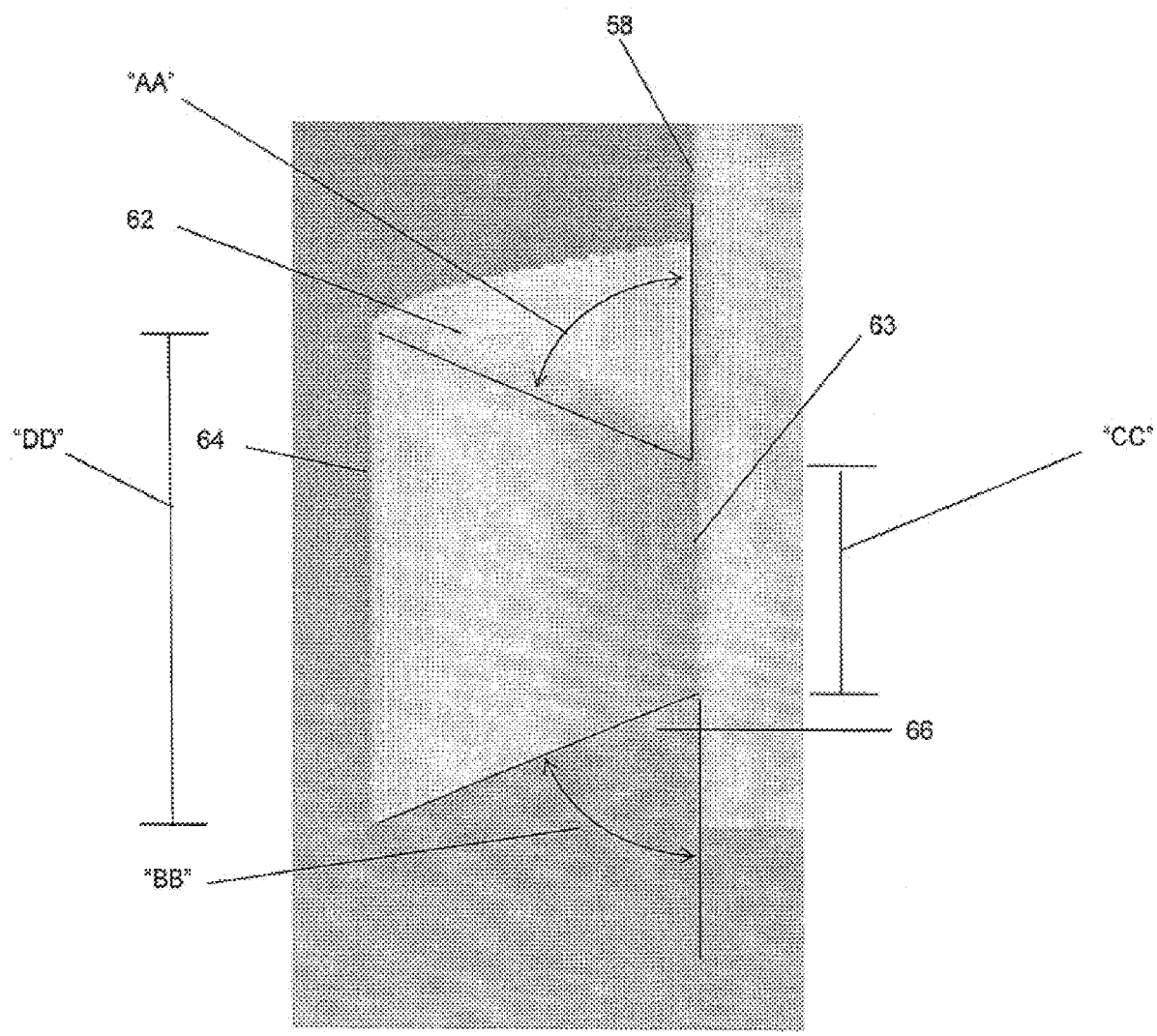
FIG. 3A illustrates a magnified view of a thread component.

As illustrated in FIG. 3A, thread component 60 may also include thread base surface 63. In certain embodiments, thread base surface 63 is generally continuous with outer core body surface 58. In other embodiments, thread base surface 63 is a surface from outer core body surface 58, but may alternatively be attached to outer core body surface 58.

The angle between upper thread surface 62 and outer core body surface 58 is upper thread angle "AA." The angle between lower side thread surface 66 and outer core body surface 58 is lower thread angle "BB." In certain embodiments, upper thread angle "AA" is between 45 and 90 degrees and lower thread angle "BB" is between 45 and 90 degrees. In certain embodiments, upper thread angle "AA" and/or lower thread angle "BB" is 60 degrees.

As also illustrated in FIG. 3A, length "CC" of thread base surface 63 may be 0.102 millimeters (mm), 0.300 mm, or 0.700 mm. In certain embodiments, length "DD" of outer thread surface 64 is 0.318 mm, 0.875 mm, or 1.275 mm at its widest point. Of course, length "DD" of outer thread surface 64 may be shorter or longer, e.g., near the upper or lower sections of core body element 54. As some examples, the ratio of length "CC" of thread base surface 63 to length "DD" of outer thread surface 64 may be 0.102 mm:0.318 mm, 0.300 mm:0.875 mm, or 0.700 mm:1.275 mm.

In certain embodiments, the size of thread component 60 is static throughout the entire thread component 60. In other embodiments, thread base surface 63 and outer thread surface 64 is smaller in length near thread termination end 67A and larger in length near thread origination end 67B (see FIG. 1). The length of each thread component surface may increase continuously (e.g. taper continuously) throughout the length of thread component 60 or may increase more sharply only near thread origination end 67B. Such embodiments are configured to permit locking of thread component 60 into thread receiving element 84 (shown in FIG. 5) when the larger portion of thread component 60 meets with or is compressed into thread receiving element 84.

Figure 3B:
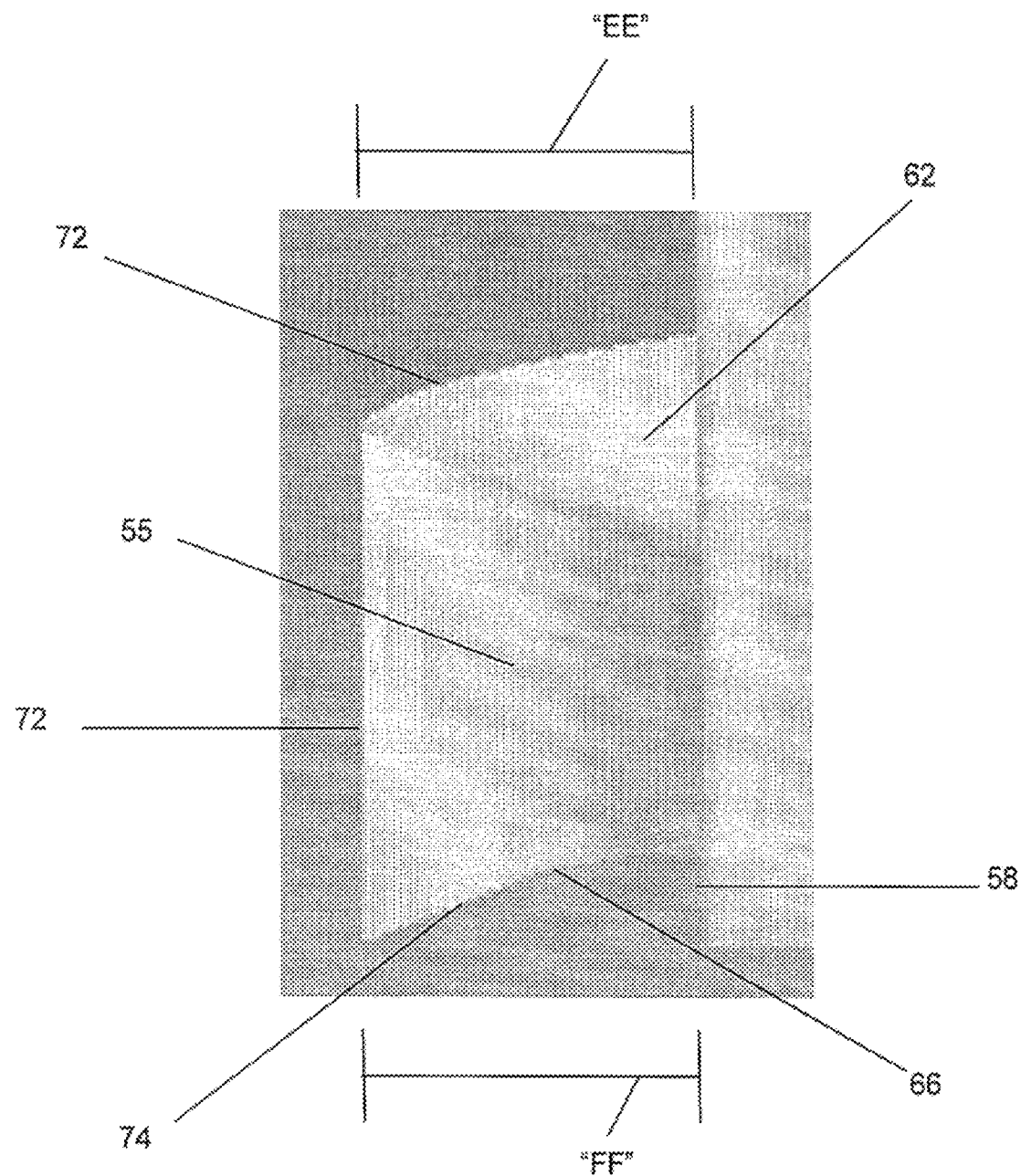
FIG. 3B also illustrates a magnified view of a thread component.

As illustrated in FIG. 3B, certain embodiments of upper thread depth "EE" between upper thread edge 72—that is, the edge at which upper thread surface 62 meets outer core body surface 58 may be 0.188 mm or 0.498 mm. Also, lower thread depth "FF" between lower thread edge 74—that is, the edge at which lower side thread surface 66 meets outer core body surface 58—may be 0.188 mm or 0.498 mm. Upper thread depth "EE" may be equal to, greater than, or less than the lower thread depth "FF."

Upper thread surface 62, lower thread surface 66, and outer thread surface 64 together form thread profile 55 (from the side view). In certain embodiments, thread profile 55 of thread component 60 may be shaped in a dovetail shape. In certain embodiments of the present invention, any surface, including upper thread surface 62, lower thread surface 66, outer thread surface 64, may be linear or curved.

Figure 4:
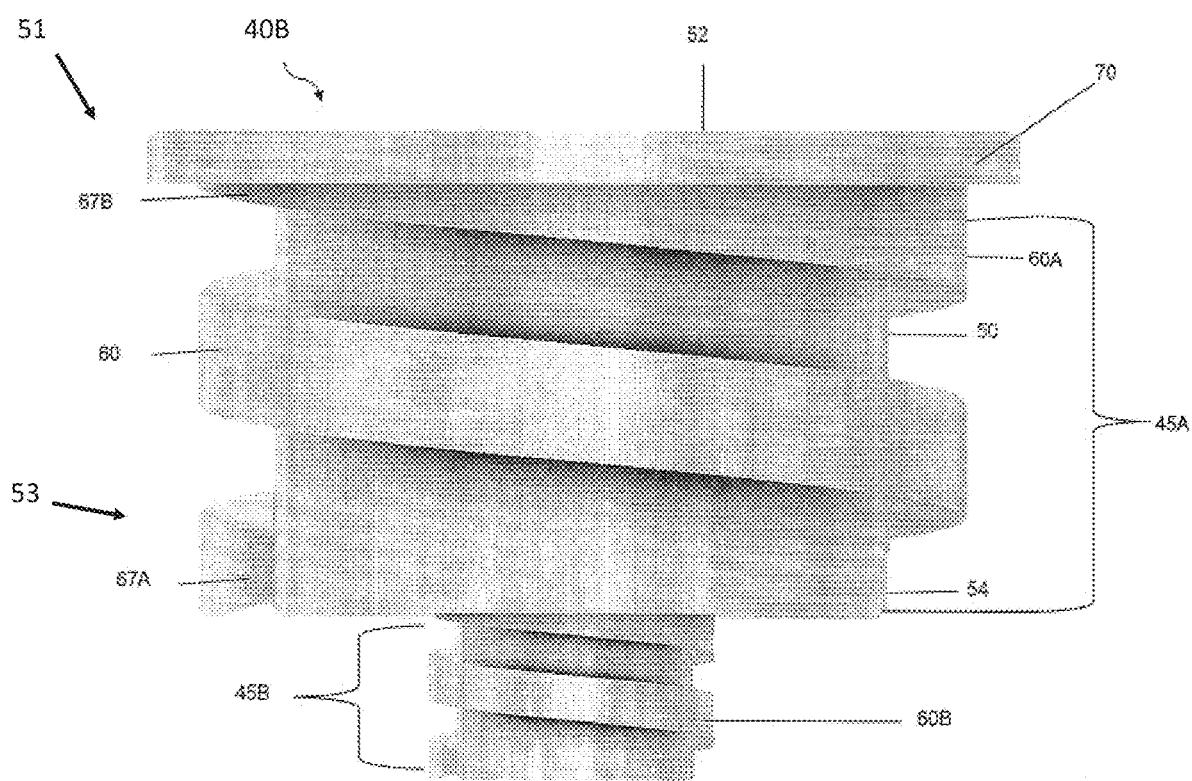
FIG. 4 illustrates an embodiment of a second interacting element having a first body component and a second body component.

Turning to FIG. 4, second body component 40B is depicted in the form of fastener 70 and includes first body component 45A and second body component 45B. Second body component 45B, including second thread component 60B, is configured to have a smaller cross-section diameter than the cross-section diameter of first body component 45A, including first thread component 60A. First body component 45A includes proximal end 51 and distal end 53 positioned adjacent to second body component 45B. Such embodiments may be configured in which first body component 45A is configured to interact with first thread receiving element 84A of plate 80 and second body component 45B is configured to interact with an object 40C (e.g., bone 41 of the patient). For example, plate 80 (see FIG. 14A) may be positioned relative to bone 41 to promote healing of bone 41. In such embodiments, fastener 70 may be partially secured within bone 41 prior to positioning plate 80, such that second thread component 60B is at least partially engaged with and received within bone 41. In this configuration, plate 80 may then be slidably disposed between distal end 53 of first body component 45A and bone 41.

In an embodiment, second thread component 60B of second body component 45B may be any size or shape, including dovetail, rounded, v-shaped, pedicle, or other. In certain embodiments, second thread component 60B has the same pitch as the pitch of first thread component 60A of first body component 45A. In other embodiments, second thread component 60B has a greater pitch than first thread component 60A, such that plate 80 may be compressed against object 40C as core body component 54 engages with plate 80. An example of a pitch measurement of certain embodiments includes a 1.25 mm pitch on first interacting element 40A (or plate 80). Such an embodiment may have a lateral surface length of 5 mm. The pitch of second thread component 60B of second body component 45B may influence the pitch of first thread component 60A on first body component 45A.

In certain embodiments, first thread component 60A may be continuous with or connected to second thread component 60B via a thread-thread connector (not shown). The thread-thread connector may have a tapered shape. In other embodiments, first thread component 60A and second thread component 60B are completely integrated and have no connection.

FIG. 5 illustrates a cross-section of an example of plate 80, such as that used for setting bone 41. Plate 80 may include end cap receiving element 82 and thread receiving element 84. End cap receiving element 82 may be generally complementary to the size and shape of end cap 52. Thread receiving element 84 may be generally complementary to the size and shape of thread component 60.

Each thread receiving element 84 may include outer receiving surface 85, upper receiving surface 86, inner receiving surface 87, and lower receiving surface 89. In certain embodiments of the present invention, any surface, including outer receiving surface 85, upper receiving surface 86, inner receiving surface 87, and lower receiving surface 89 may be linear or curved.

Figure 7:
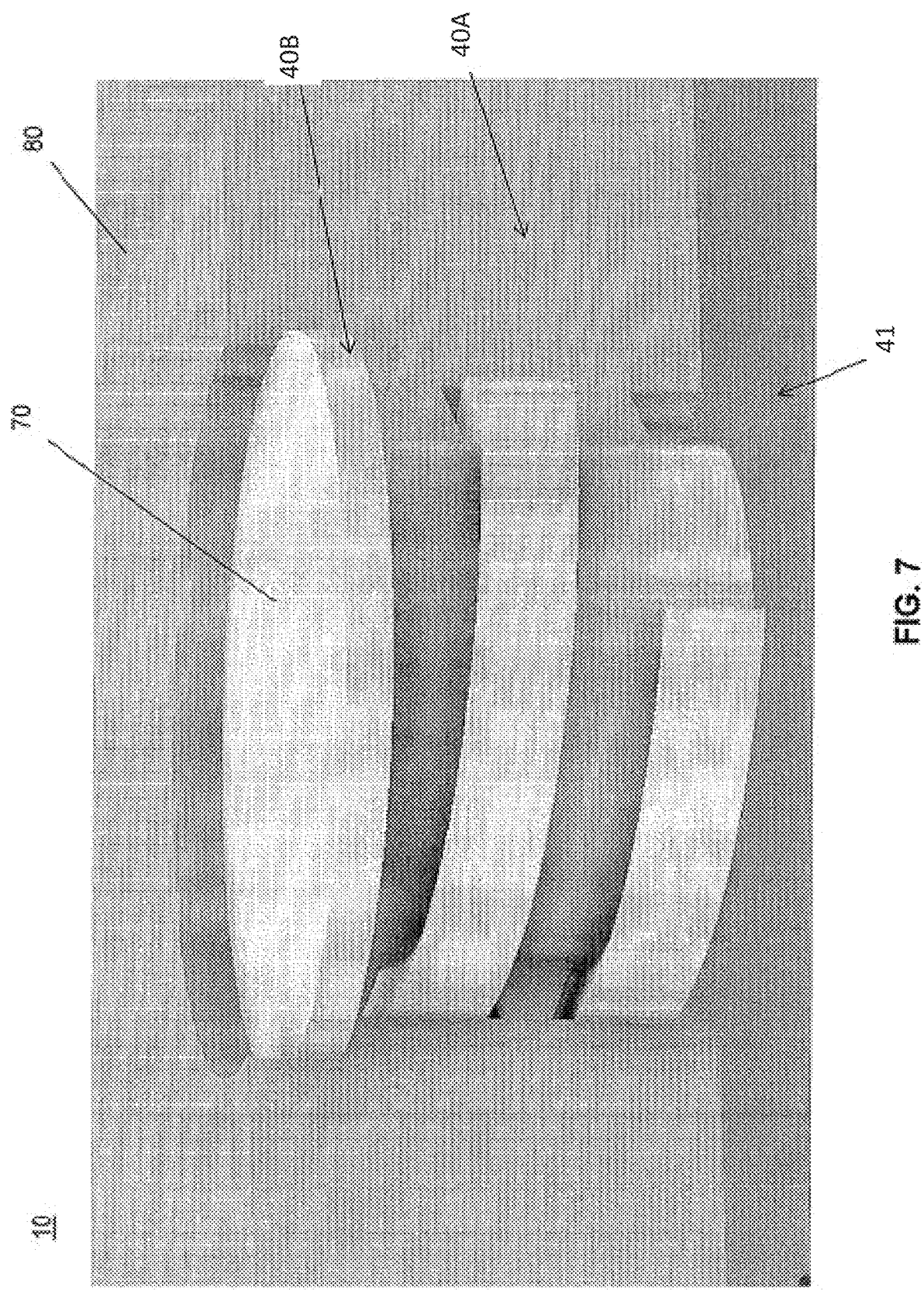
FIG. 7 illustrates a second interacting element positioned relative to a first thread receiving element of a first interacting element.

When thread component 60 is received within thread receiving element 84 (as illustrated in FIG. 7), outer receiving surface 85 is generally adjacent to or flush with outer core body surface 58 of core body 54, upper receiving surface 86 is generally adjacent to or flush with lower thread surface 66, inner receiving surface 87 is generally adjacent to or flush with outer thread surface 64, and lower receiving surface 89 is generally adjacent to or flush with upper thread surface 62.

In embodiments in which thread component 60 includes multiple helical turns, thread receiving element 84 may include more than one thread receiving element 84, such as first thread receiving element 84A, second thread receiving elements 84B, and third thread receiving element 84C. Any number of thread receiving elements 84 are contemplated. In the embodiment illustrated in FIG. 5, first thread receiving element 84A is positioned closest to first surface 90 of plate 80. Third thread receiving element 84C is positioned closest to second surface 92 of plate 80. Second thread receiving element 84B is positioned between first thread receiving element 84A and third thread receiving element 84C. In an embodiment, thread receiving element 84 may be tapered in size such that the respective portion of thread component 60 may be stabilized in position. In certain embodiments, the one or more thread receiving elements 84 are positioned along the lateral surface 94 of plate 80, such that only certain portions of thread component 60 are enclosed within thread receiving element 84. One or more thread receiving elements 84 may be flanked by first lateral surface 94A and second lateral surface 94B of plate 80.

Figure 6A:
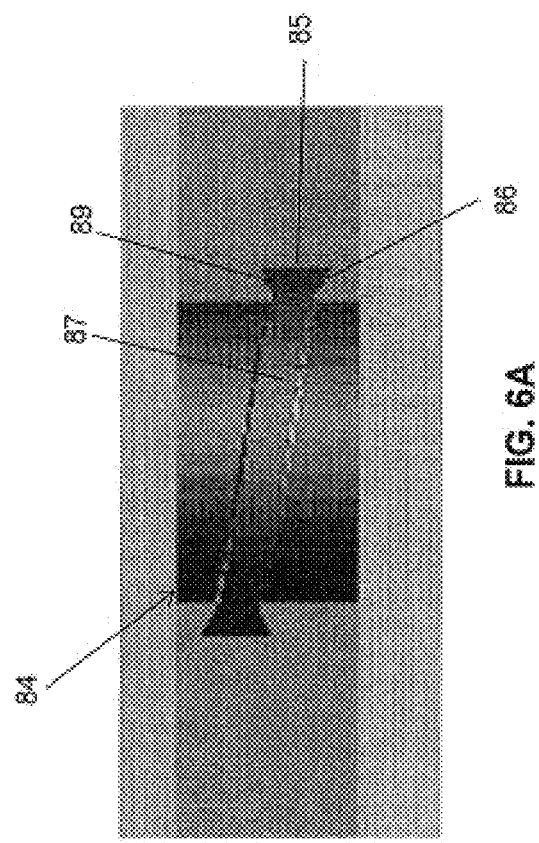
FIG. 6A illustrates a side view of an embodiment of a first interacting element in the form of a plate, including a thread receiving element.
Figure 6B:
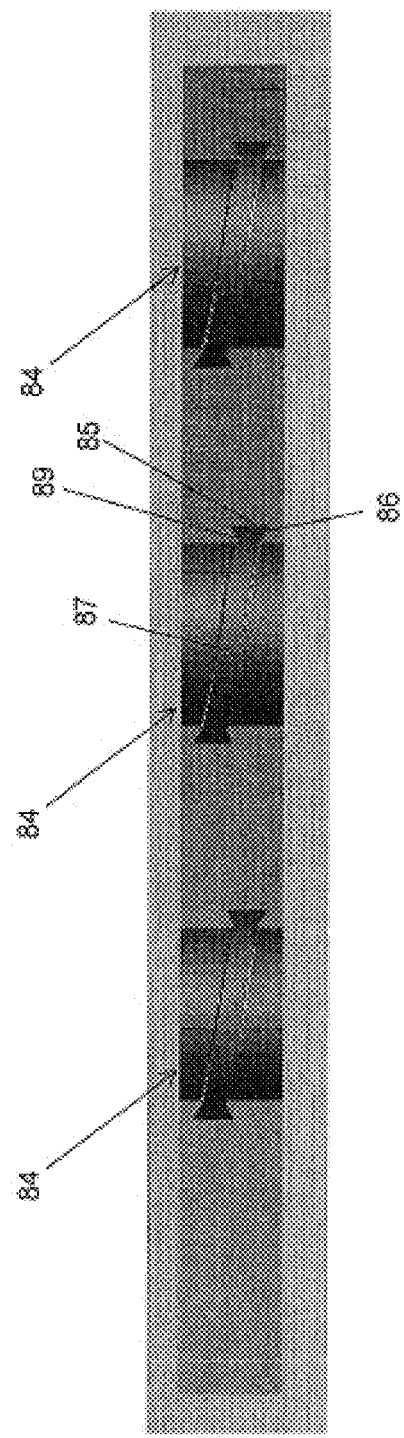
FIG. 6B illustrates a side view of an embodiment of a first interacting element in the form of a plate, including a plurality of thread receiving elements.
Figure 6C:
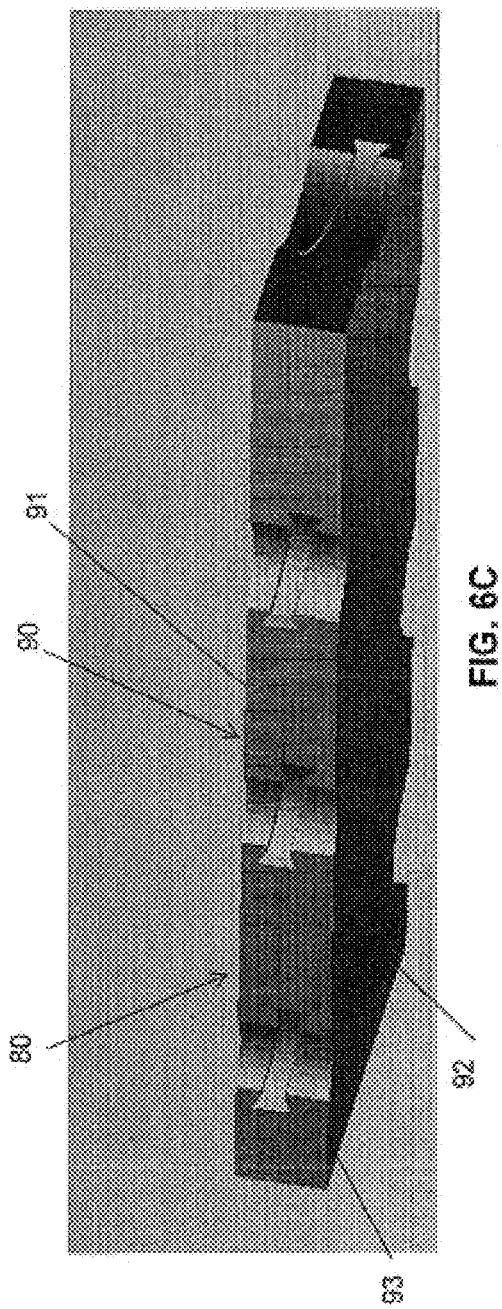
FIG. 6C illustrates a perspective view of an embodiment of a first interacting element in the form of a plate, including a plurality of thread receiving elements.
Figure 6D:
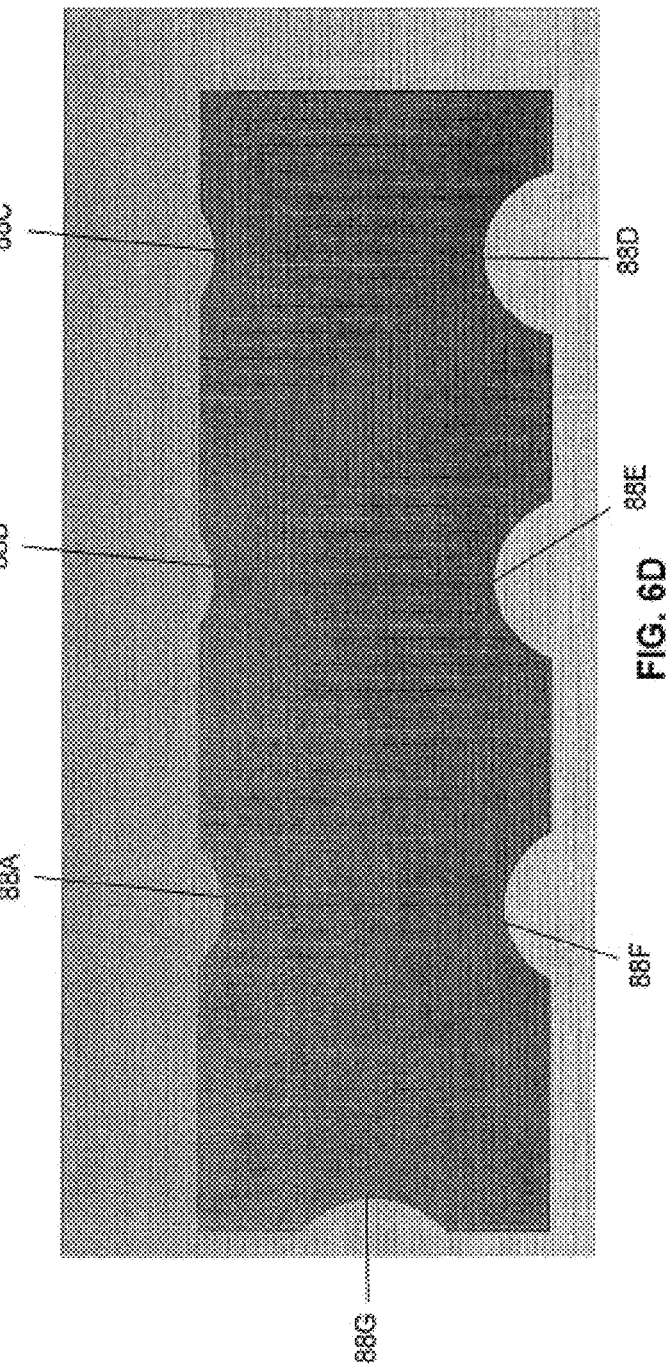
FIG. 6D illustrates a top view of an embodiment of a first interacting element in the form of a plate, including a plurality of thread receiving elements.

Lateral surfaces 94A and 94B meet with first surface 90 at upper edge 91 and second surface 92 at lower edge 93. The distance between the first surface 90 and second surface 92 results in thickness 95. Additional embodiments may be configured to include only one thread receiving element 84, such as that illustrated in FIG. 6A. Certain other embodiments of plate 80 according to the invention include more than one thread receiving element 84 as illustrated in FIGS. 6B-6D. Embodiments of thread receiving element 84 shown in FIGS. 6A-6D may receive thread component 60 shaped in multiple helical turns, for example, turns that start at or near the bottom side of first body component 45A and end at or near the top side of first body component 45A.

Alternatively, thread receiving element 84 embodiments shown in FIGS. 6A-6D may receive thread component 60 shaped in a single helical turn or less than a full helical turn. For purposes of this application, a "full helical turn" is a complete 360-degree rotation around a cylindrical axis. (Similarly, if the rotation was in a flat plane instead of a cylindrical axis, the shape would be a circle, not a helix.)

FIG. 6D shows examples of shape configurations of thread receiving element 84, or more specifically, top profile 88 of thread receiving element 84. In an embodiment, top profile 88 may form a general arc-shape configuration. In certain embodiments, the arc-shape configuration may be any portion of a circle from 360-degrees to 90-degrees, including, for example, a three-quarters-circle shape (270-degrees), half-circle-shape (180-degrees), third-circle shape (120-degrees), or fourth-circle shape (90-degrees). While the embodiment in FIG. 6D illustrates multiple thread receiving elements 84, each having a different arc-shape configuration 88A-88G, it is contemplated that plate 80 may include a plurality of thread receiving elements 84 each having the same arc-shape configuration.

FIG. 7 illustrates assembly 10, including fastener 70, configured positioned within plate 80 for setting bone 41. In an embodiment fastener, 70 may be configured to interact with both plate 80 and bone 41. In certain embodiments, fastener 70 may be configured to interact with only plate 80. In certain other embodiments fastener, 70 may be configured to only interact with bone 41 (i.e., without the use of plate 80).

Figure 8A:
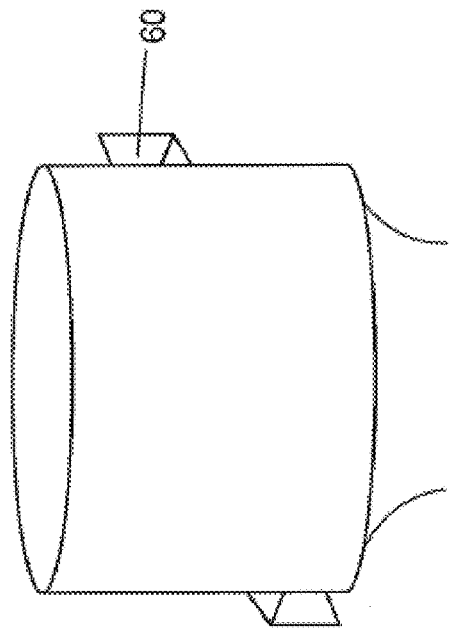
FIG. 8A illustrates an embodiment of a second interacting element having a first body component and a second body component, wherein the thread component on the first body component includes only a partial turn of a helix.
Figure 8B:
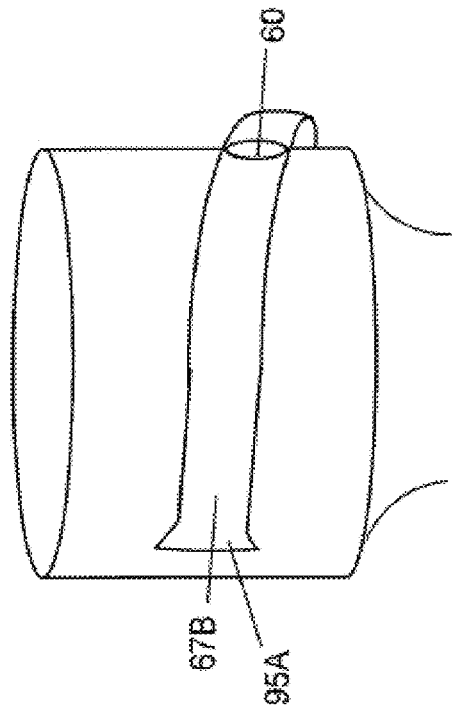
FIG. 8B illustrates an embodiment of a second interacting element having a first body component and a second body component, wherein the thread component on the first body component includes only a partial turn of a helix.
Figure 8C:
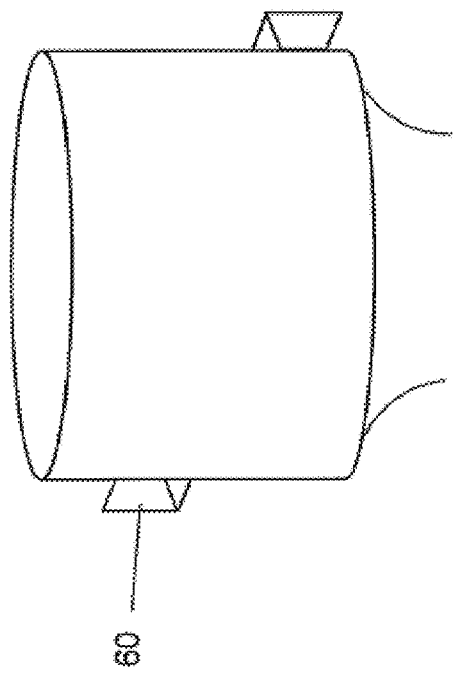
FIG. 8C illustrates an embodiment of a second interacting element having a first body component and a second body component, wherein the thread component on the first body component includes only a partial turn of a helix.
Figure 8D:
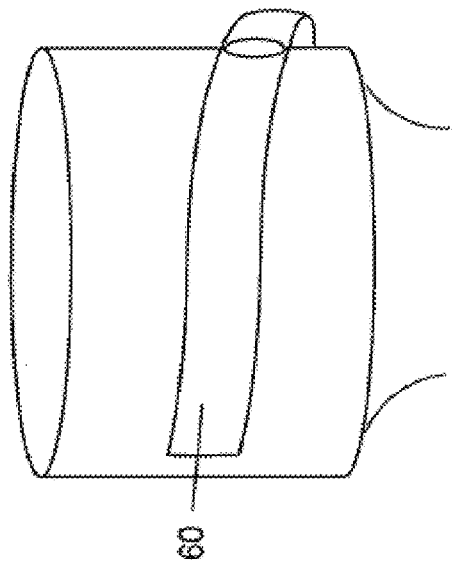
FIG. 8D illustrates an embodiment of a second interacting element having a first body component and a second body component, wherein the thread component on the first body component includes only a partial turn of a helix and the thread component includes a stop element.

As illustrated in FIGS. 8A and 8B, the helical shape of thread component 60 may be left-handed or right-handed. Also illustrated in FIGS. 8A-8D, thread component 60 may be sized to include only a partial turn of a helix shape. As also illustrated in FIG. 8D, thread origination end 67B may include an enlarged portion to form stop 95A such that thread component 60 cannot move further into thread receiving component 84.

Figure 9A:
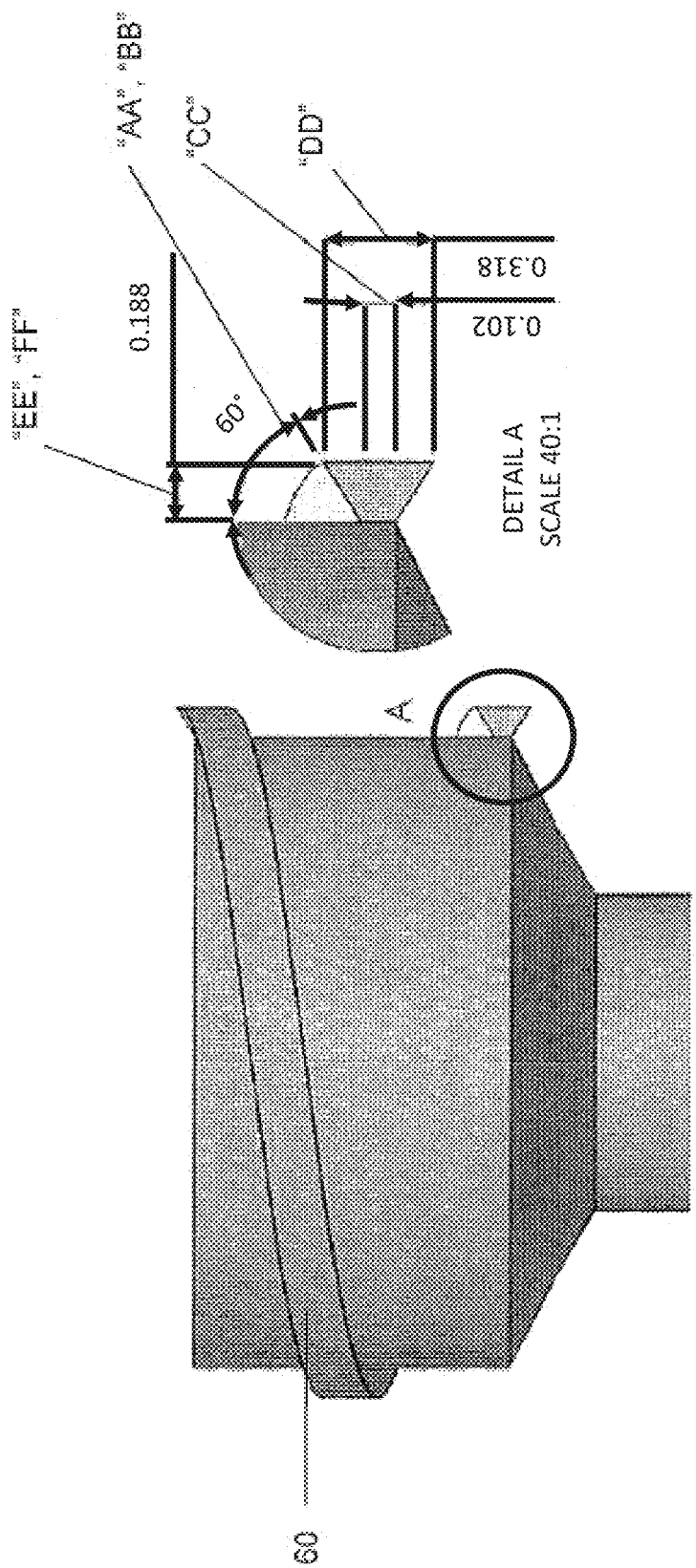
FIG. 9A illustrates an embodiment of a second interacting element having a first body component and a second body component.
Figure 9B:
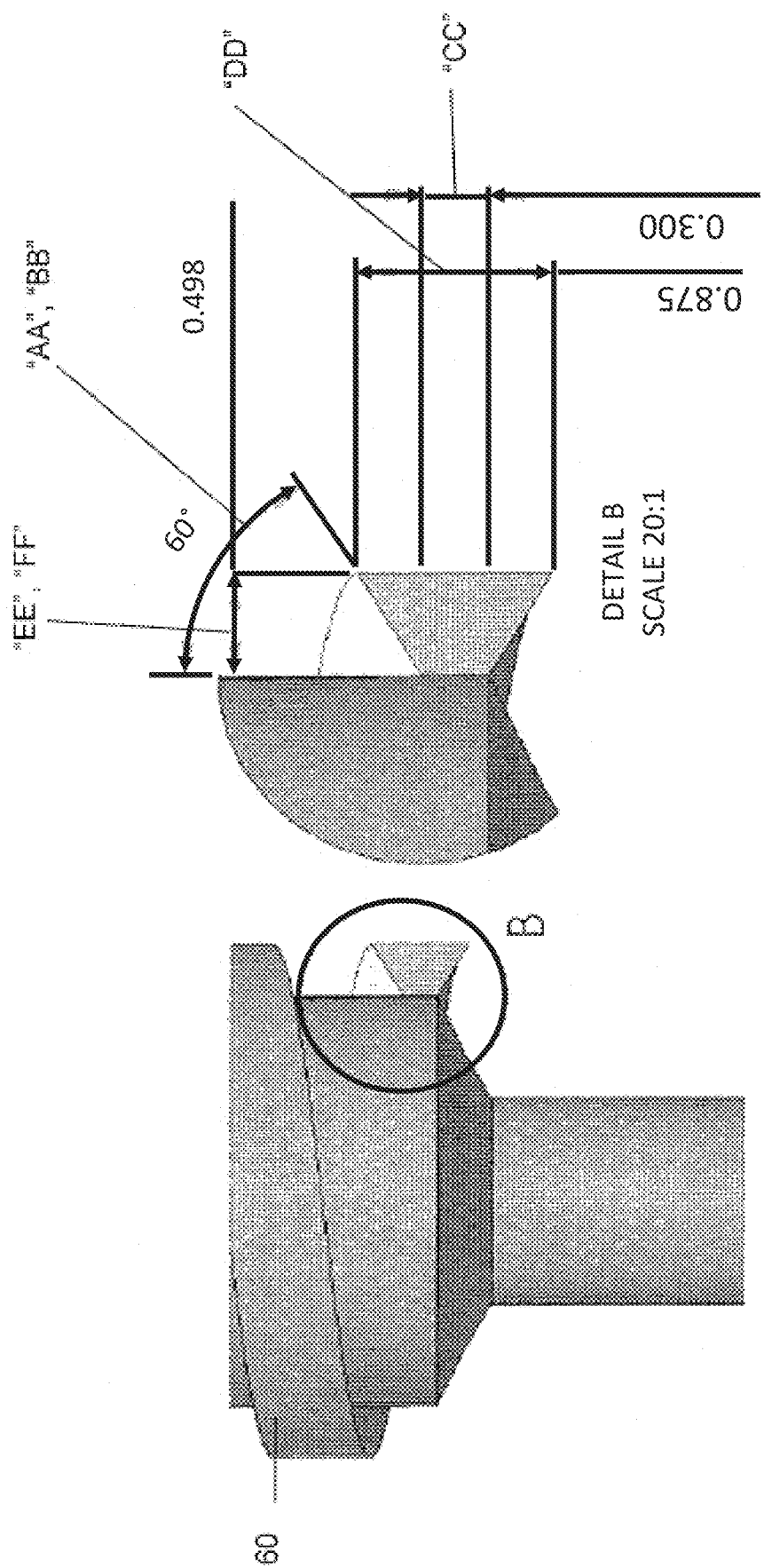
FIG. 9B illustrates an embodiment of a second interacting element having a first body component and a second body component.
Figure 9C:
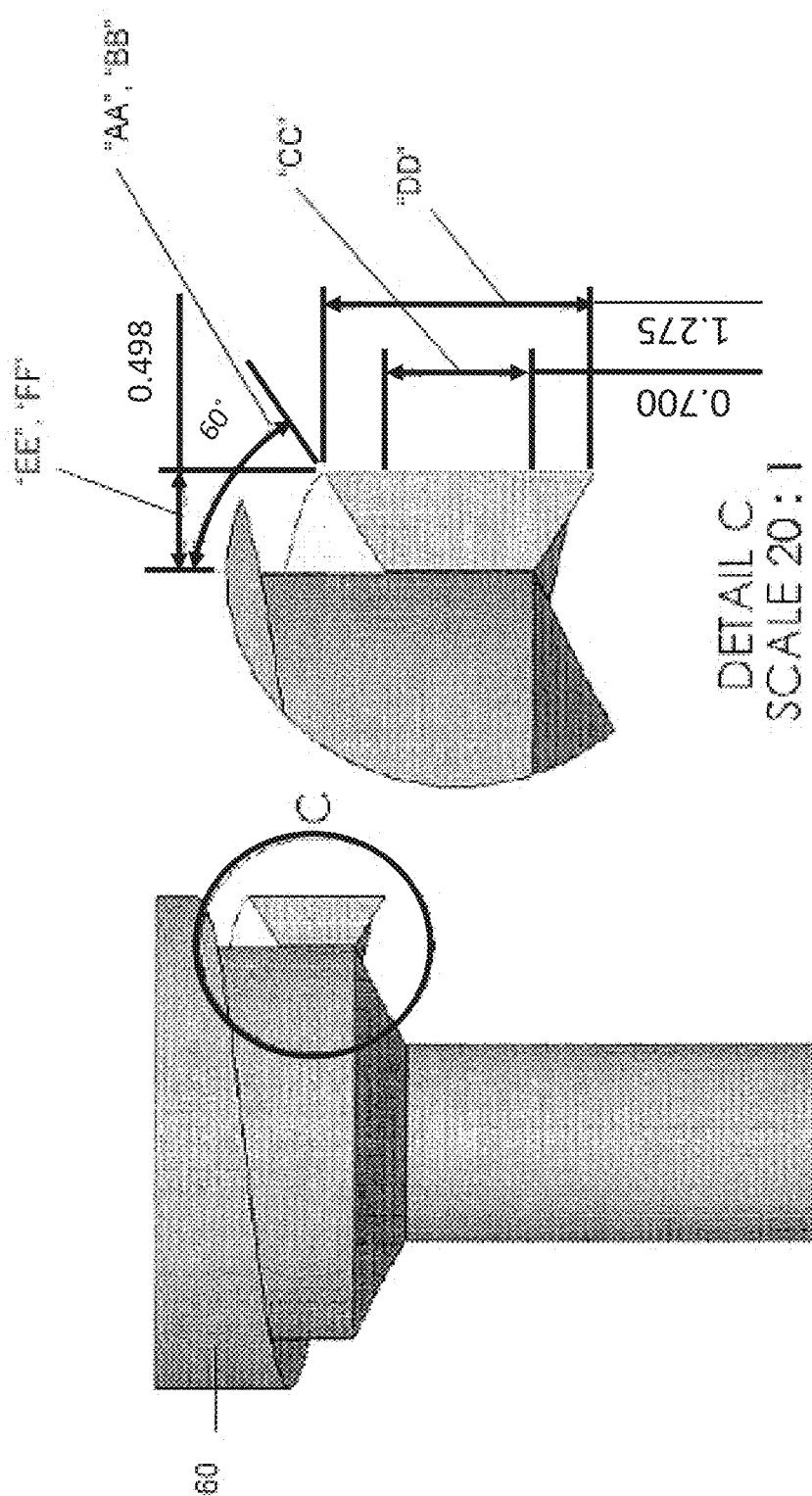
FIG. 9C illustrates an embodiment of a second interacting element having a first body component and a second body component.

FIGS. 9A-9C illustrate additional embodiments of the present invention. While certain embodiments are identified as having specific measurements in millimeters (mm), each part of the invention may be sized and shaped for any particular purpose. Specifically, in certain embodiments, measurements are scaled up or scaled down based on the ratios illustrated in FIGS. 9A-9C, sometimes for a particular purpose (e.g., stronger connection or more flexibility). In addition, the ratios between components may be altered to achieve a particular purpose as well. For example, turning to FIG. 9A, upper thread angle "AA" and/or lower thread angle "BB" may be about 60 degrees. The length of thread base surface "CC" may be about 0.102 mm and the length of outer thread surface "DD" about 0.318 mm. Upper thread depth "EE" and/or lower thread depth "FF" may be about 0.188 mm. Turning to FIG. 9B, upper thread angle "AA" and/or lower thread angle "BB" may be about 60 degrees. The length of thread base surface "CC" may be about 0.300 mm and the length of outer thread surface "DD" about 0.875 mm. Upper thread depth "EE" and/or lower thread depth "FF" may be about 0.498 mm.

In another example shown in FIG. 9C, upper thread angle "AA" and/or lower thread angle "BB" may be about 60 degrees. The length of thread base surface "CC" may be about 0.700 mm and the length of outer thread surface "DD" about 1.275 mm. Upper thread depth "EE" and/or lower thread depth "FF" may be about 0.498 mm.

Figure 10A:
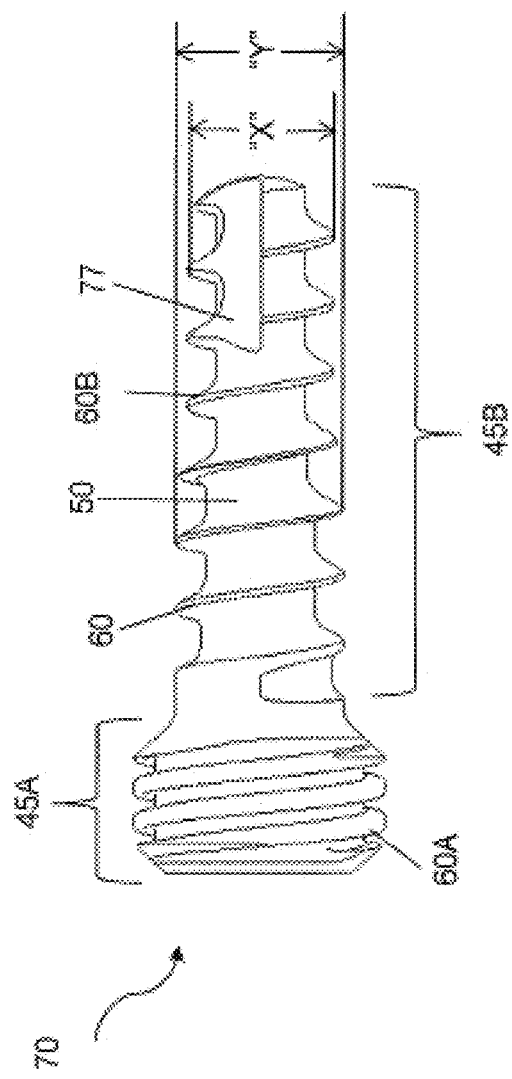
FIG. 10A illustrates an embodiment of a second interacting element having a first body component and a second body component.
Figure 10B:
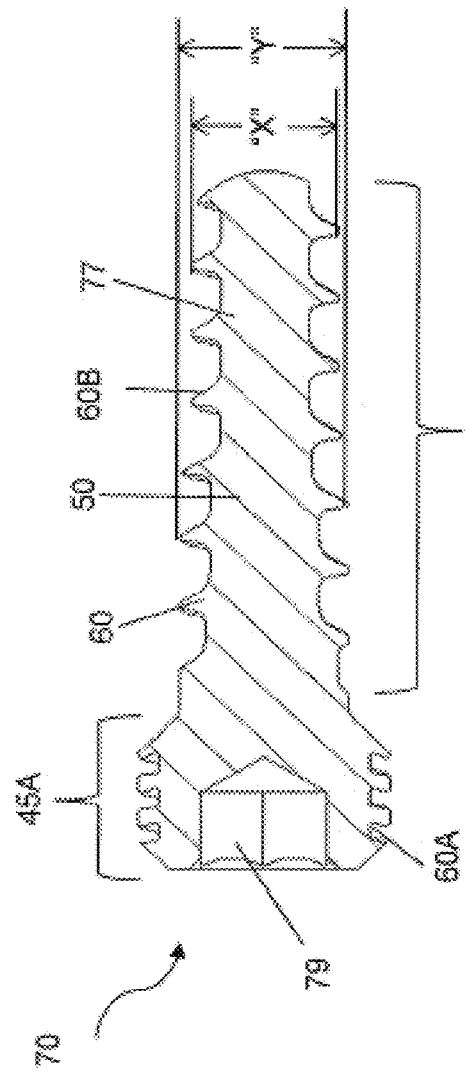
FIG. 10B illustrates a cross-sectional view of an embodiment of a second interacting element having a first body component and a second body.

FIG. 10A and FIG. 10B illustrates an embodiment of fastener 70 including body component 50 and thread component 60. In particular, fastener 70 includes first body component 45A and second body component 45B. First body component 45A includes first thread component 60A configured to interface with plate 80. Second body component 45B includes second thread component 60B configured to interface with bone 41. As shown in this embodiment, body component 50 includes different cross-sectional diameters as shown by "X" and "Y." Although two cross-sectional diameters are shown, any number of different cross-sectional diameters of body component 50 is contemplated. Body component 50 with a varying cross-sectional diameter provides for optimum anchoring of assembly 10 to bone 41. Also shown in this embodiment is cutting flute element 77 to facilitate a self-tapping capability. As shown within first body component 45A, hex component 79 allows for manipulation and placement of fastener 70 by using a hex socket. As shown more particularly in FIG. 10B, thread component 60A includes a one-sided dovetail thread arrangement with variable pitch.

Figure 11B:
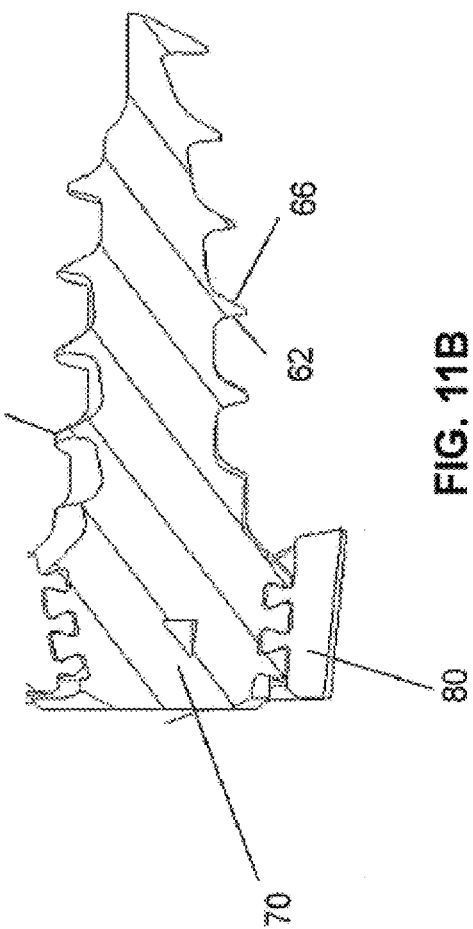
FIG. 11B illustrates an embodiment of the second interacting element, in the form of a fastener, engaged with the thread receiving element of the first interacting element.
Figure 11A:
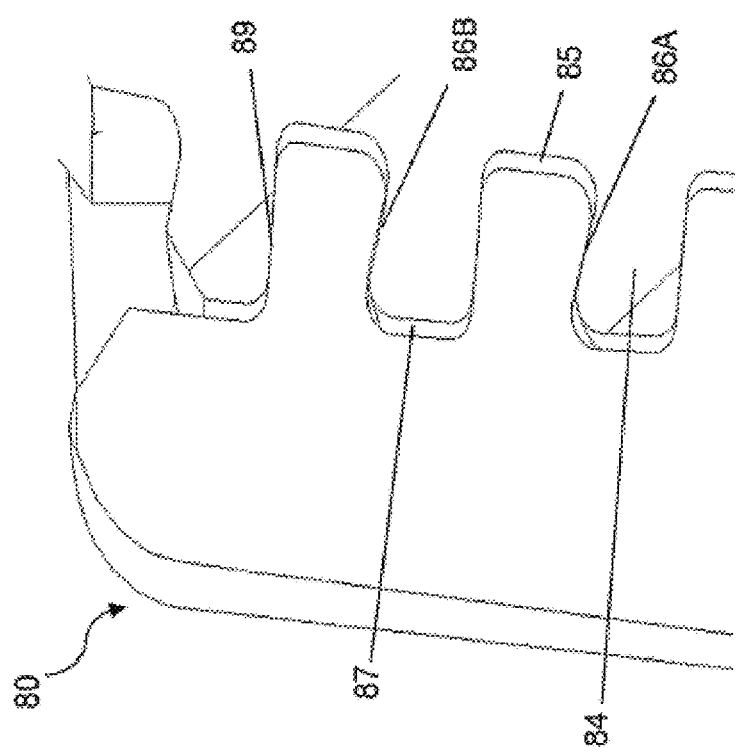
FIG. 11A illustrates an exploded view of a plate including a thread receiving element.

FIG. 11A illustrates an exploded view of plate 80 including thread receiving element 84. Each thread receiving element 84 includes outer receiving surface 85, upper receiving surface 86, inner receiving surface 87, and lower receiving surface 89. In this particular embodiment, upper receiving surface 86A is of a different pitch than upper receiving surface 86B to accommodate the varying pitch of fastener 70. Thus, the first threads of fastener 70 engage upper receiving surface 86A of thread receiving element 84 of plate 80 have a sliding fit. In contrast, the last threads of fastener 70 engage upper receiving surface 86B of receiving element 84 of plate 80 have an interference fit to lock plate 80 and fastener 70 together as shown more specifically in FIG. 11B. FIG. 11B illustrates a cross-sectional view of an embodiment of fastener 70 engaged with thread receiving element 84 of plate 80. Fastener 70 shown in FIG. 11B has two-sided dovetail threads 60, i.e., upper thread surface 62 and lower thread surface 66 are each of a dovetail shape.

FIGS. 12A-12C illustrate a first interacting element in the form of plate 80 according to an embodiment of the invention. As shown, plate 80 includes one or more apertures 71 in which fasteners 70 threadably engage with thread receiving element 84. FIG. 12B illustrates lordotic curve 75 and FIG. 12C illustrates endplate curve 76, both of which coincide or match the curvature of certain features of an endplate or spine.

Figure 12D:
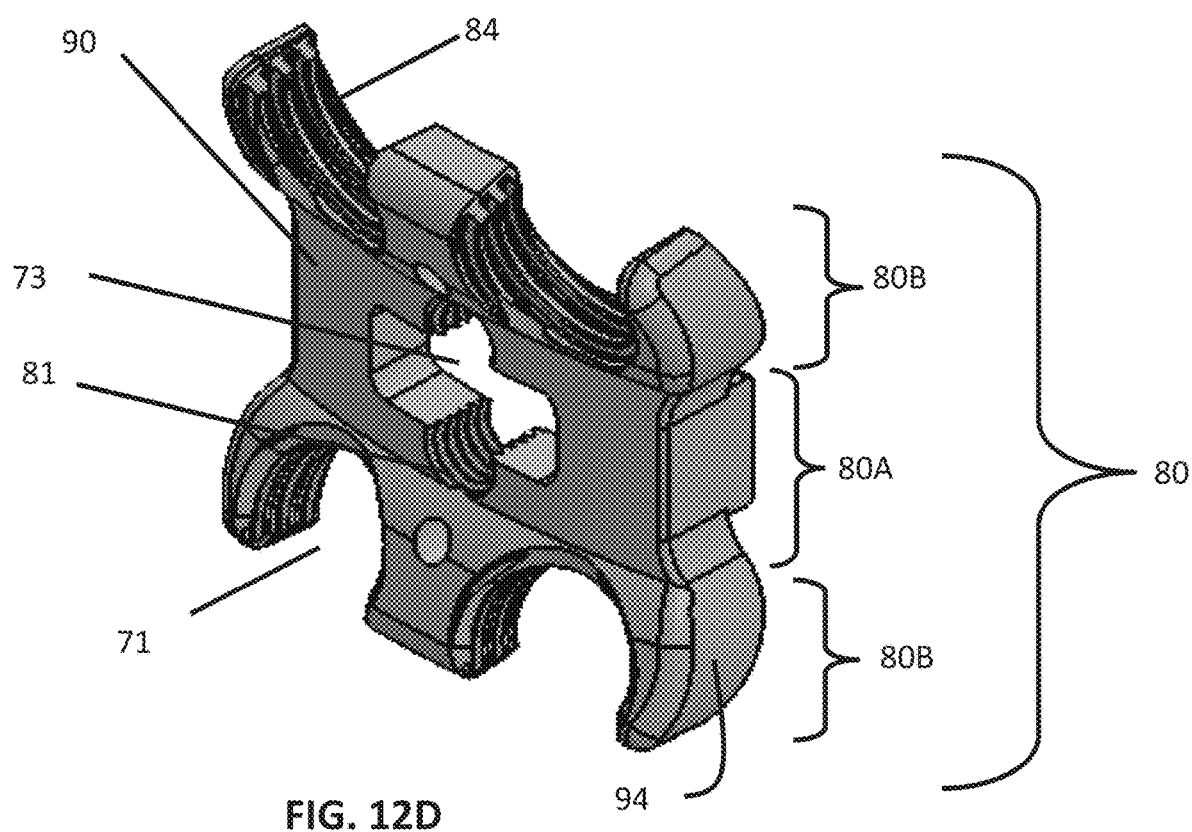
FIG. 12D illustrates a perspective view of an embodiment of a first interacting element.
Figure 12E:
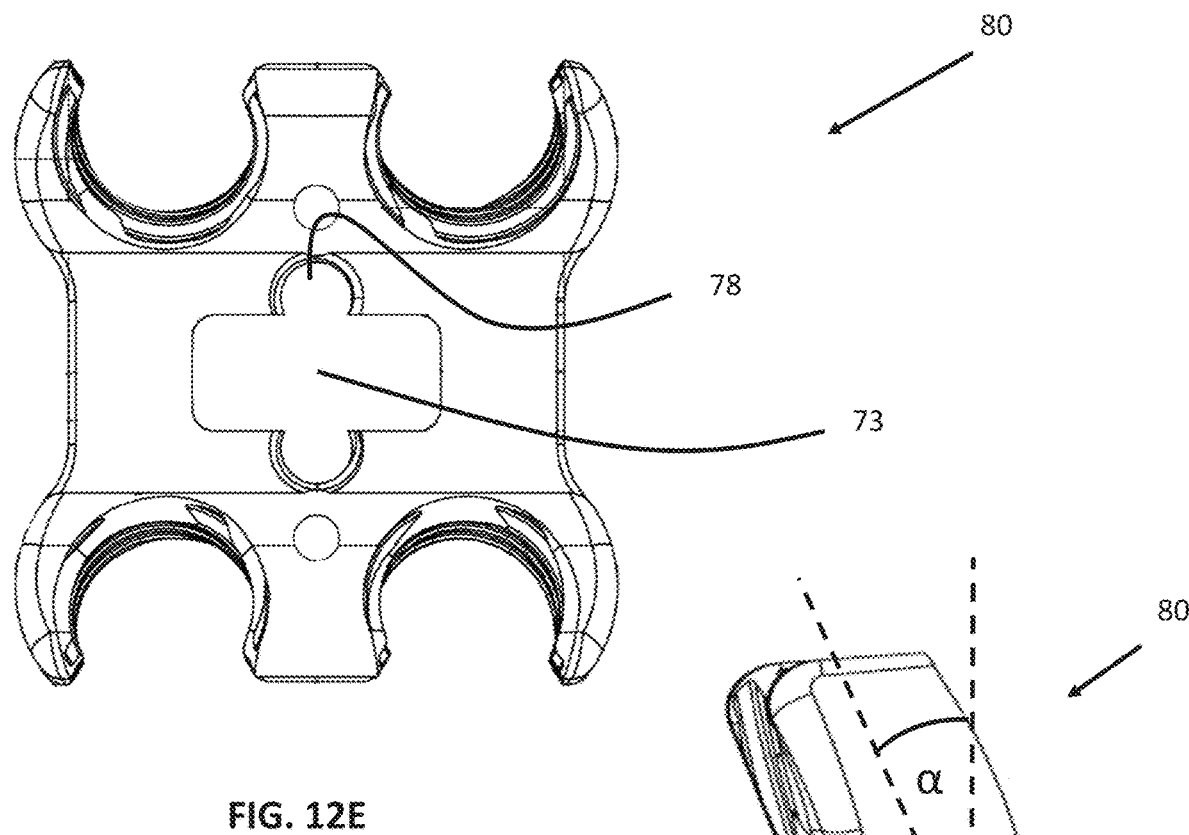
FIG. 12E illustrates a top view of an embodiment of a first interacting element.
Figure 12F:
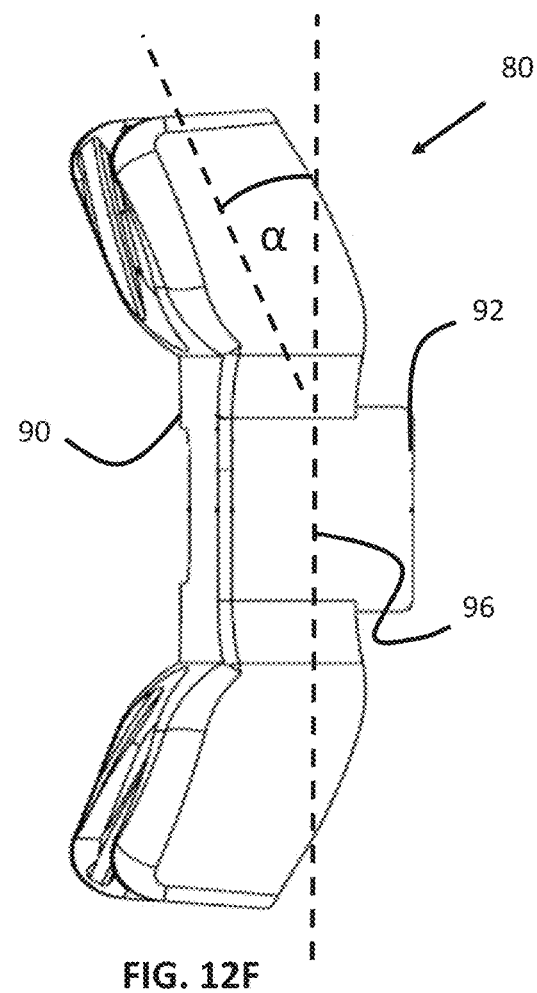
FIG. 12F illustrates a side view of an embodiment of a first interacting element.

In an embodiment, as shown in FIGS. 12D-12F, plate 80 includes plane 96 disposed parallel to upper plate body surface 90 and lower plate body surface 92. Plate 80 includes body portion 80A and a pair of fastening cantilevers 80B bent out of plane 96 at angle α, each fastening cantilever 80B is positioned on opposite sides of body portion 80A and include one or more apertures 71 disposed therein. Fastening cantilevers 80B are disposed at angle α in relation to plane 96 to ensure that when fasteners 70 engage thread receiving elements 84 of apertures 71, fasteners 70 are angled away from an edge of bone 41, thereby reducing the risk of bone 41 splintering.

In an embodiment angle α is between 5-30 degrees. When α is greater than 5 degrees, the fastener is unlikely to splinter the bone and when α is less than 30 degrees, the fastener is unlikely to contact any fasteners secured to an adjacently located plate secured on an opposite end of the bone. In an embodiment, angle α is between 12-22 degrees. When α is between 12 and 22 degrees, there is even less chance of splintering the bone or contacting other fasteners from adjacent assemblies. In an embodiment, angle α is 17 degrees. When a fastener engages a bone at about 17 degrees, the chance of splintering the bone or contacting other fasteners from adjacent assemblies is reduced to a minimum.

An embodiment of plate 80 includes a viewing window 73 extending through body portion 80A from first surface 90 to second surface 92 and provides for intra-operative as well as post-operative visualization of the anatomical structure behind plate 80. Intra-operative visualization may include, for example, visualization of a bone graft, surgical tools, or other surgical implements during a surgical procedure, such as an end plate attached to plate 80 via fastener 70. Post-operative visualization may include, for example, visualization on x-rays subsequent to the surgical procedure.

Figure 12G:
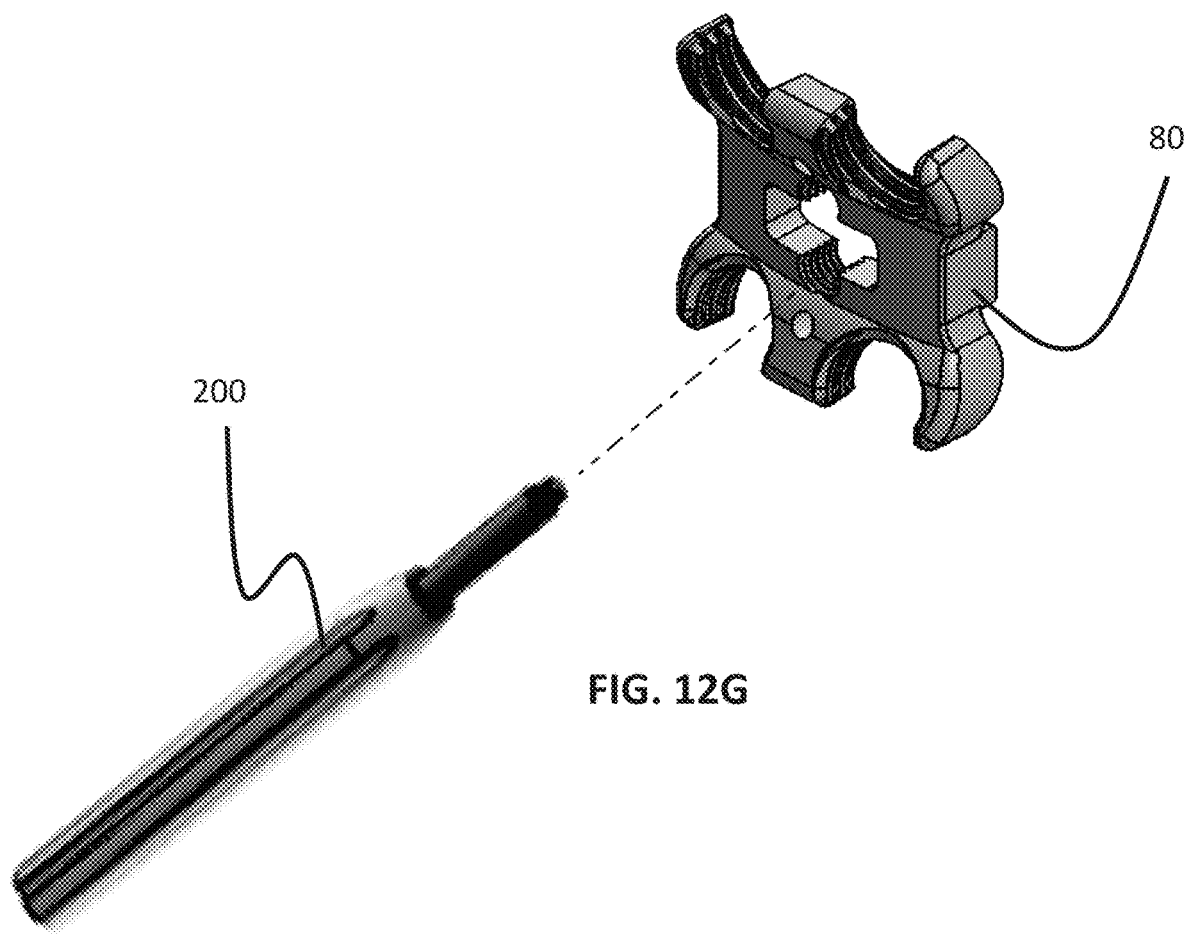
FIG. 12G illustrates an exploded view of a handle depicting where the attachment of the handle would occur on an embodiment of a first interacting element.

FIGS. 12D-12F depict an embodiment in which viewing window 73 includes one or more engagement apertures 78 having threads 81 configured to threadably receive threaded engagement portion 219 of handle 200 (see e.g., FIGS. 18A-18C). Coupling of handle 200 with engagement apertures 78 provides an increase in control and manipulation of plate 80 during surgery as depicted in FIG. 12G.

Figure 13A:
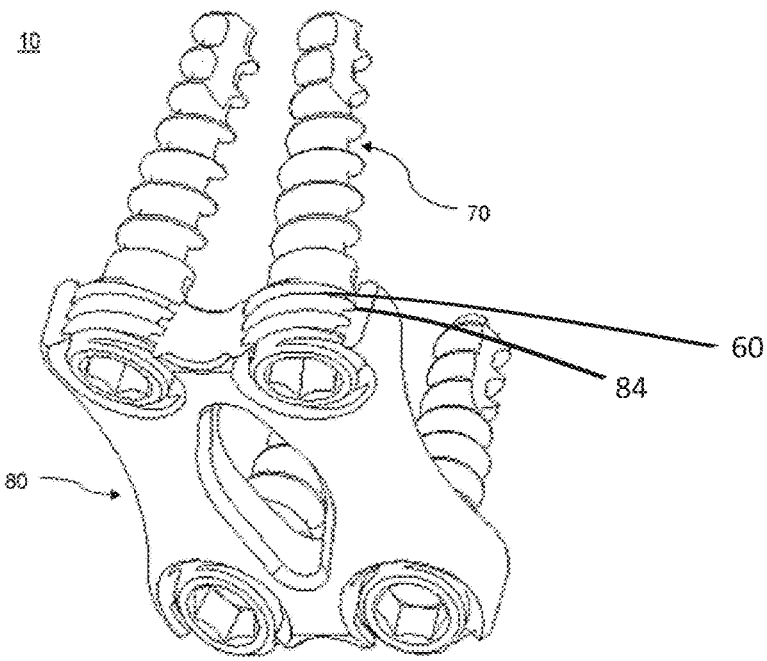
FIG. 13A illustrates an assembly view of a first interacting element in the form of a plate and having a plurality of second interacting elements in the form of fasteners disposed within apertures of the first interacting element.
Figure 13B:
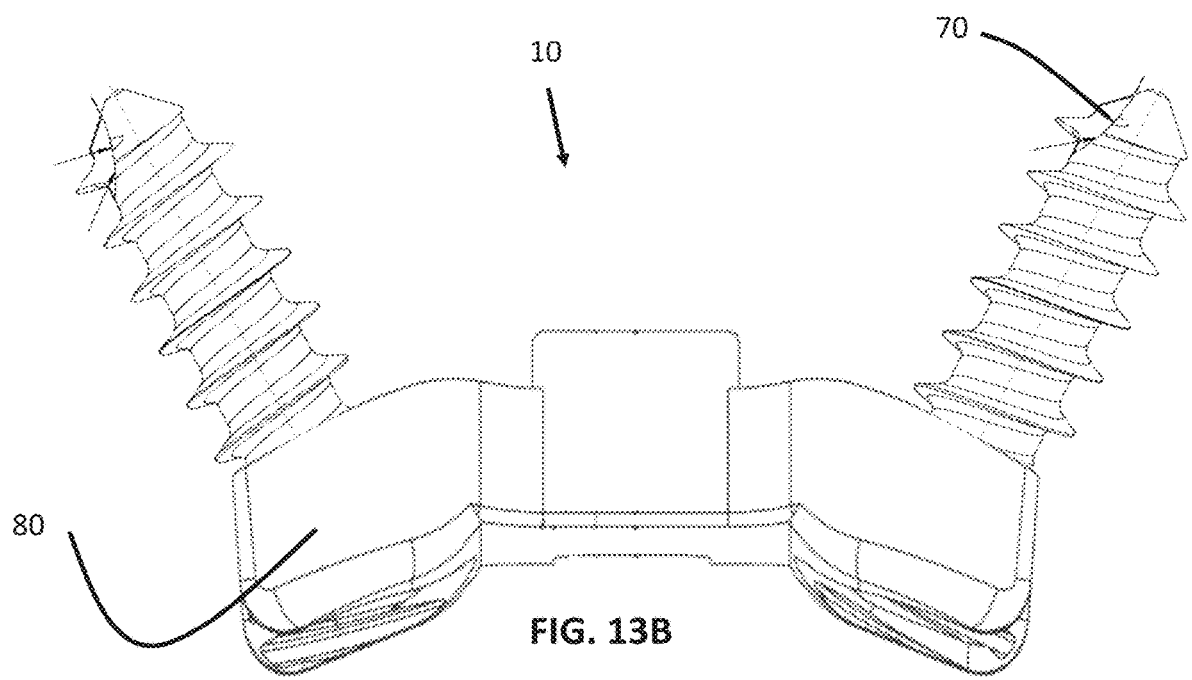
FIG. 13B illustrates an assembly view of an alternative embodiment of a first interacting element and a plurality of second interacting elements.
Figure 14B:
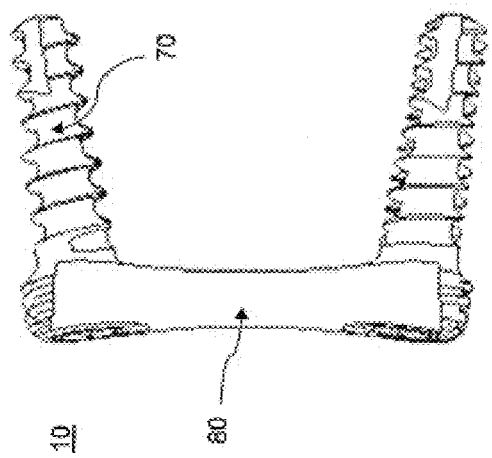
FIG. 14B illustrates a horizontal side view of the assembly shown in FIG. 13A.
Figure 14C:
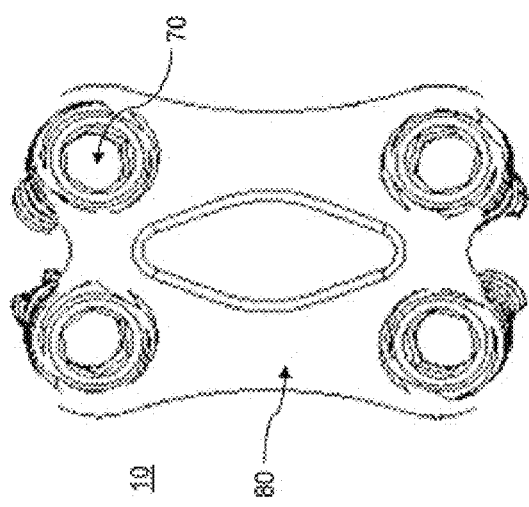
FIG. 14C illustrates a top view of the assembly shown in FIG. 13A.
Figure 14A:
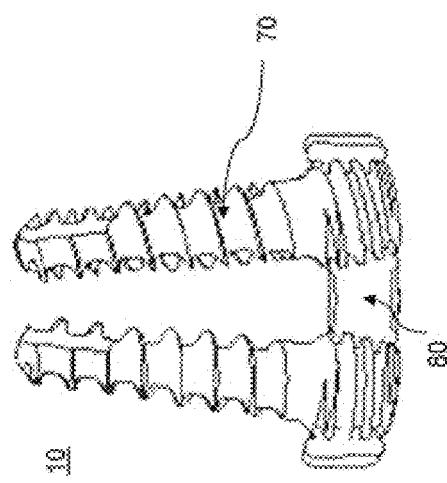
FIG. 14A illustrates a longitudinal side view of the assembly shown in FIG. 13A.

FIG. 13A illustrates assembly 10, including plate 80 and a plurality of fasteners 70 threadably secured within apertures 71. The trajectories of fasteners 70 can be seen in FIGS. 13A-13B and FIGS. 14A-14C. FIG. 14A illustrates a cross-sectional side view of assembly 10, FIG. 14B illustrates a side view of assembly 10 and FIG. 14C illustrates a top view of assembly 10. Fasteners 70 are driven with a hex socket until they are flush with plate 80. In particular, the embodiments depicted illustrate apertures 71 surrounding approximately 70% of end cap 52 of fastener 70 leaving the superior-most and inferior-most parts of fasteners 70 exposed. This low-profile embodiment allows for secure engagement between fasteners 70 and plate 80, which reduces the risk of pain and discomfort.

As previously discussed in relation to FIG. 6, an embodiment of plate 80 includes apertures 71 that are incomplete/semi-circular apertures in which the incomplete section of the circumference is an opening in a lateral surface of the first interacting element. This feature is best depicted in FIGS. 5-6 and 12 showing the first interacting element in the form of plate 80. When the circumferential opening is located in an outer lateral surface of the plate, the size of plate 80 is inherently reduced. In addition, the circumferential opening in the lateral surface of plate 80 enables a user to first secure fastener 70 and then move the plate in a lateral manner such that the circumferential opening receives the already secured fastener 70. Fastener 70 can then be rotated so that the threads engage the thread receipts in plate 80 thereby setting the location of plate 80 prior to drilling additional pilot holes or screwing additional fasteners 70 into the bone to further engage plate 80.

In an embodiment, aperture 71 may be any semi-circular shape such that the lateral opening in the circumference is greater than a diameter of at least a portion of fastener 70 to ensure that the lateral opening can receive fastener 70 when fastener 70 is already secured in an object. In an embodiment, aperture 71 may have any circumferential length that allows thread receiving element 84 of plate 80 to engage with thread component 60 of fastener 70, thereby securing fastener 70 to plate 80.

Figure 15A:
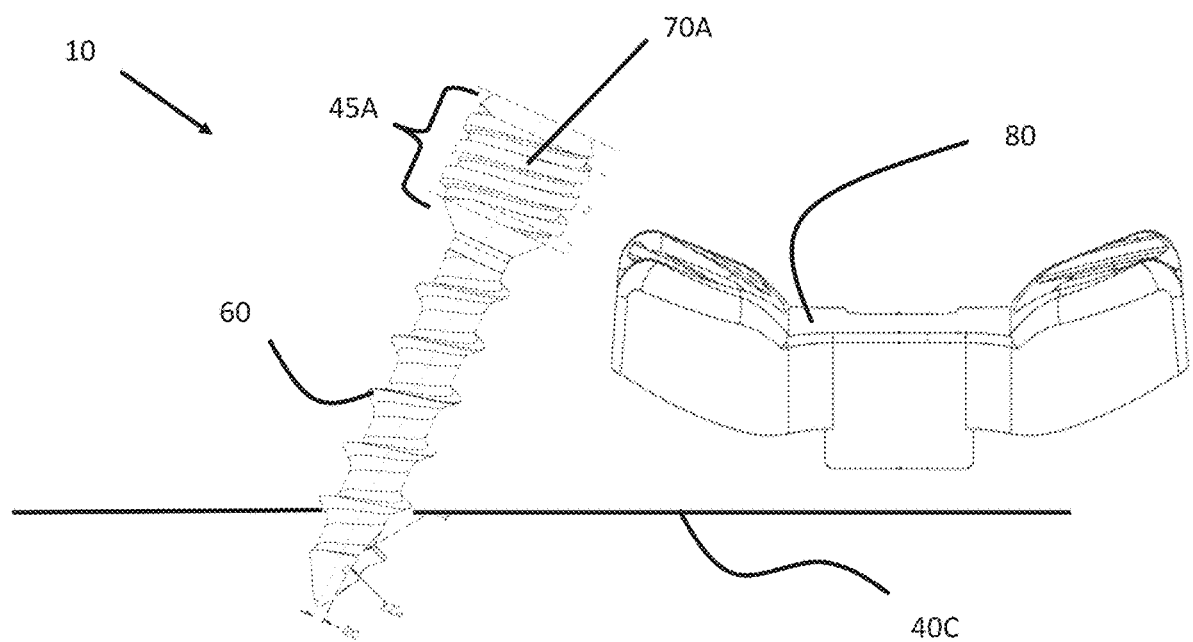
FIG. 15A illustrates a side view of a second interacting element in the form of a fastener partially disposed within the surface of a bone and the first interacting element of in the form of a plate uncoupled from the second interacting element.
Figure 15B:
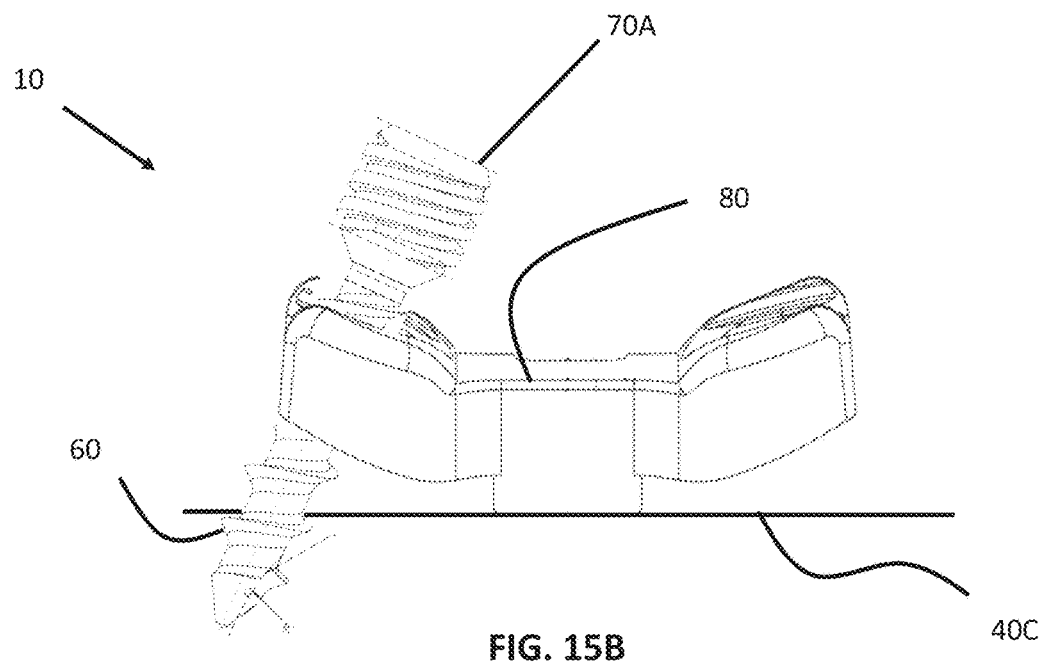
FIG. 15B illustrates a side view of a first interacting element in the form of a plate disposed between the surface of the bone and the first body component of second interacting element in the form of a fastener.
Figure 15C:
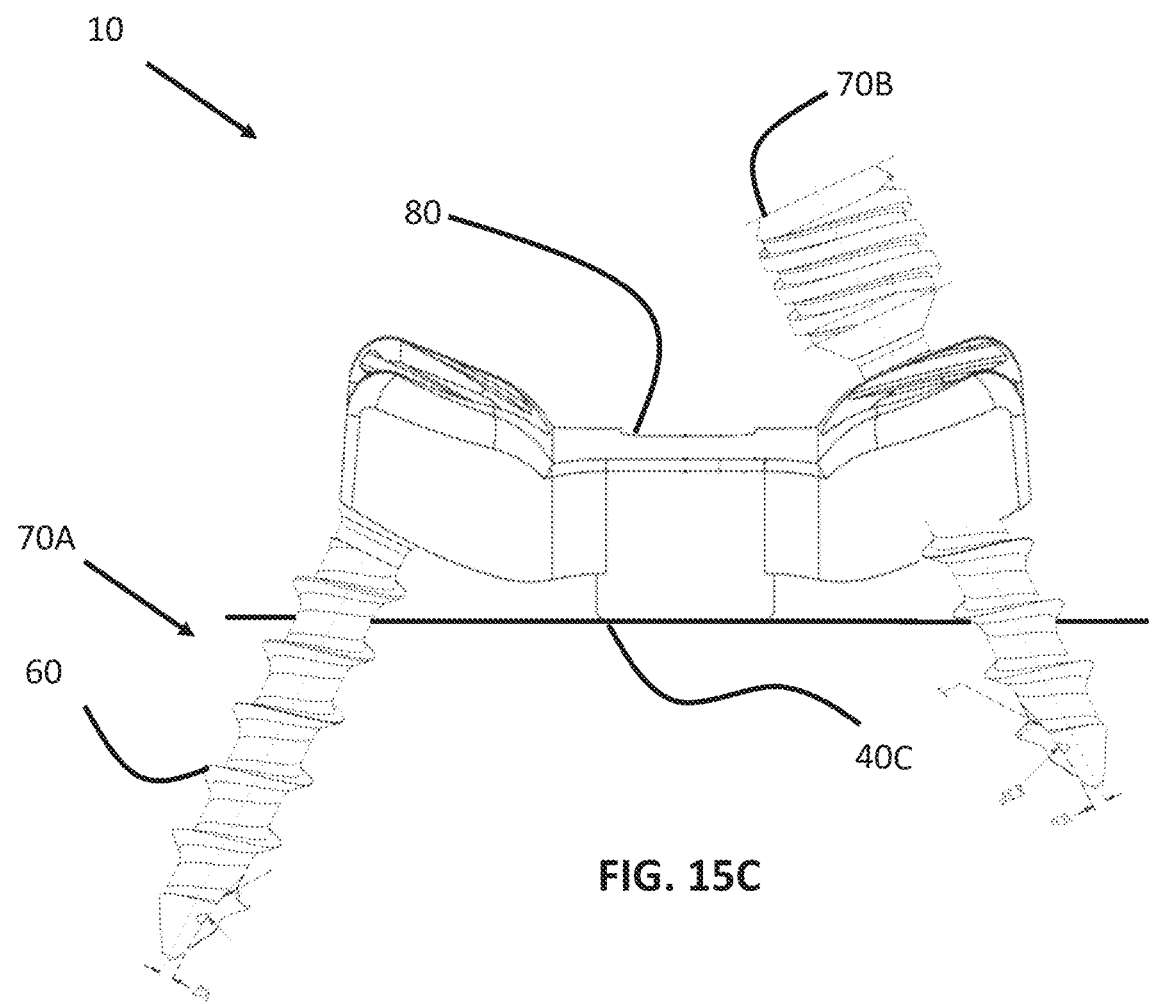
FIG. 15C illustrates an assembly secured within the surface of an object in the form of a bone.
Figure 16A:
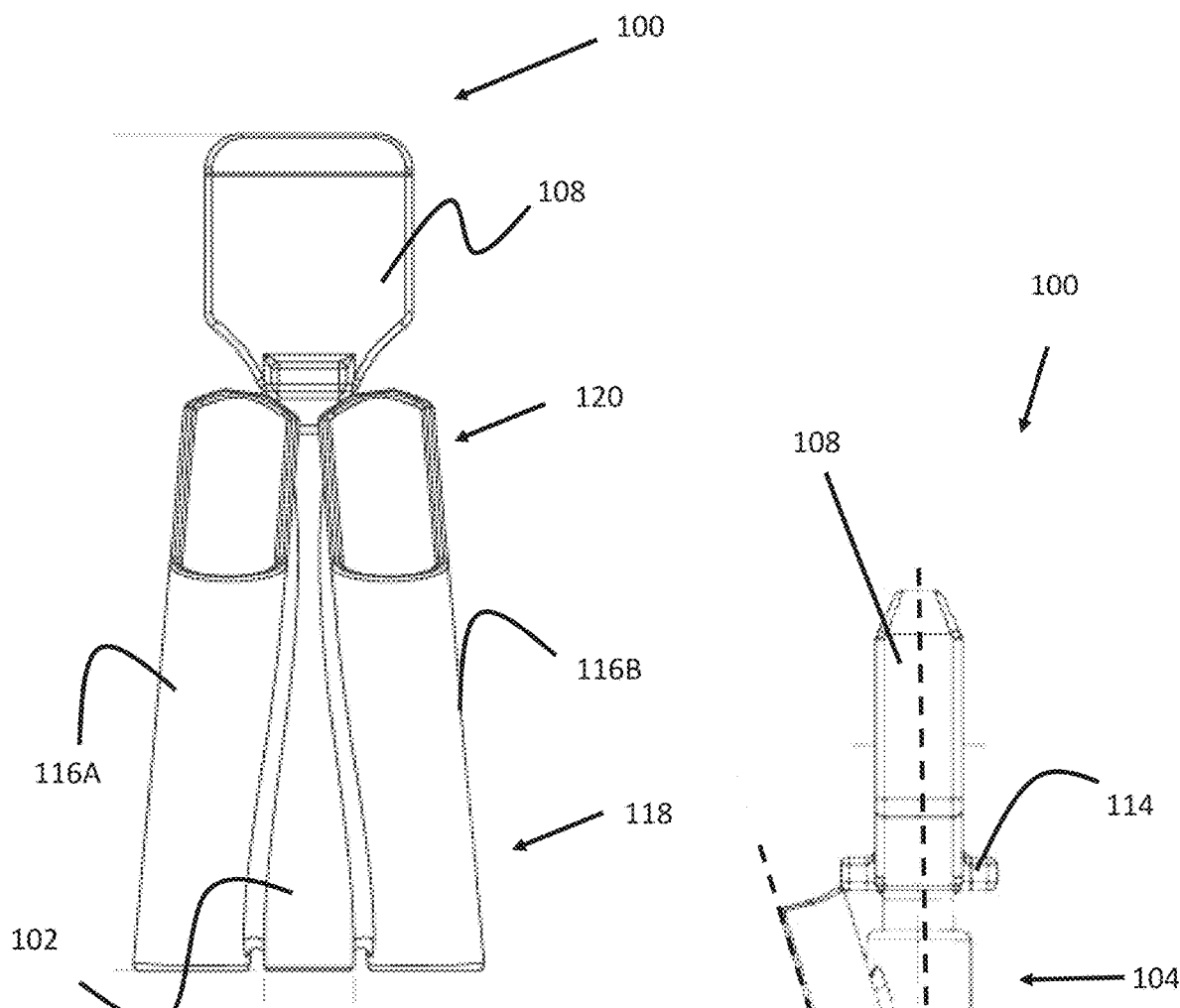
FIG. 16A illustrates a top view of a trial sizer.
Figure 16B:
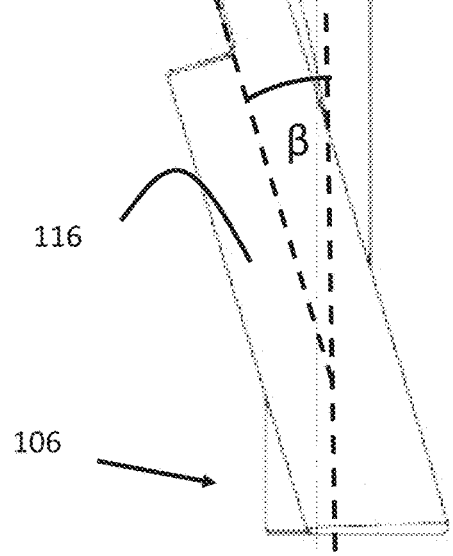
FIG. 16B illustrates a side view of a trial sizer.
Figure 16C:
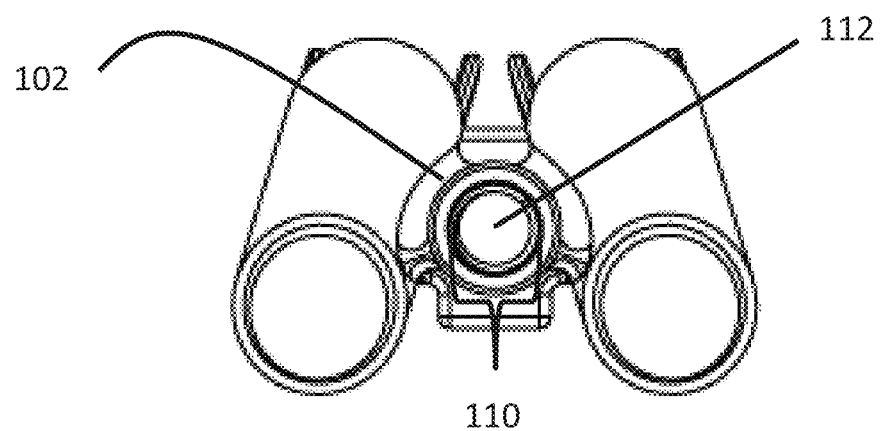
FIG. 16C illustrates a bottom view of a trial sizer.
Figure 16D:
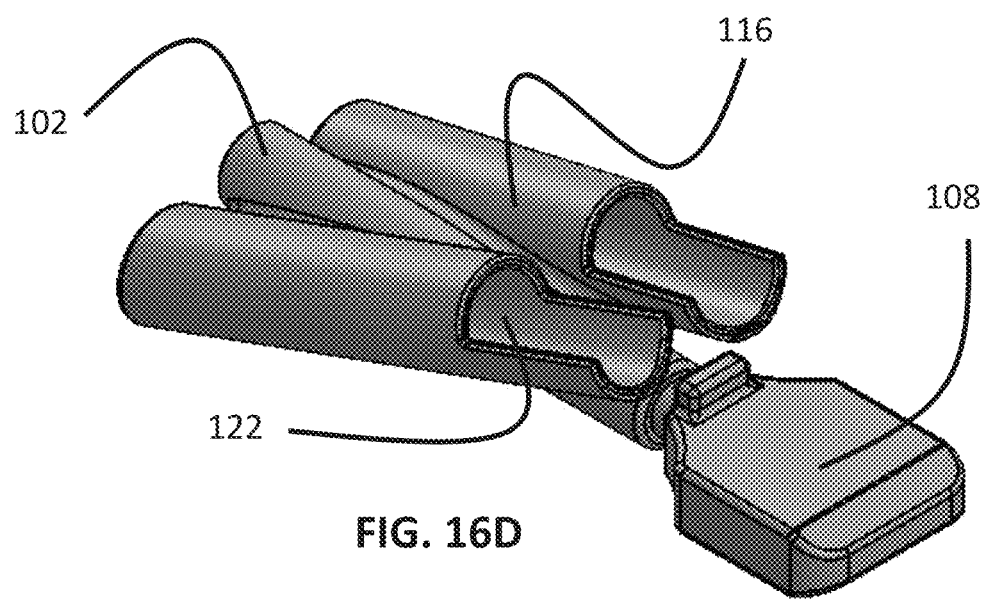
FIG. 16D illustrates a perspective view of a trial sizer.

In an embodiment of the novel method, as depicted in FIGS. 15A-15C, first fastener 70A is partially threaded into bone 41. A semi-circular aperture in plate 80 is then slidably disposed between bone 41 and distal end 53 of first body component 45A. Once the semi-circular aperture is partially encircling first fastener 70A, first fastener 70A may be driven further within bone 41, whereby first thread component 60A threadedly engages thread receiving element 84 providing for a secure engagement between first fastener 70A and plate 80 and ultimately securing plate 80 to bone 41. Following engagement of first fastener 70A with plate 80 and bone 41, additional fasteners 70B may be easily positioned with respect to plate 80. The engagement between first fastener 70A and plate 80 prevents the movement of plate 80 in the lateral, horizontal, and vertical directions. As such, subsequent fasteners 70B can be placed within apertures 71 and driven into bone 41 via the rotation of remaining fasteners 70B until first thread component 60A threadedly engages thread receiving element 84 and is locked into place within plate 80.

An embodiment of the method further includes trial sizer 100 to ensure proper alignment of fasteners 70 with respect to plate 80. An embodiment of trial sizer 100 is depicted in FIGS. 16A-16D. Trial sizer 100 is configured to assist in the drilling of one or more pilot holes within bone 41 by providing precise drilling angles and spacing for the one or more pilot holes, which ultimately receive fastener 70 when driven into bone 41. The pilot holes ensure that the spacing of the pilot holes perfectly matches the spacing and angle of apertures 71 in plate 80. Furthermore, the use of a pilot hole may further reduce the risk that bone 41 will fracture or splinter when fastener 70 is driven into bone 41.

Figure 17:
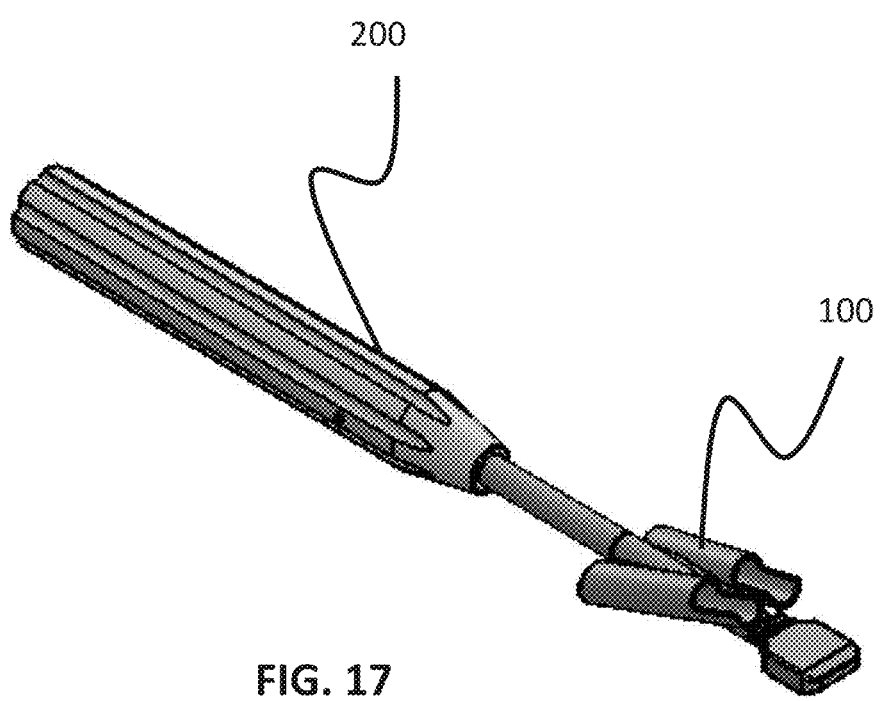
FIG. 17 illustrates a perspective view of a trial sizer coupled to a handle.
Figure 19A:
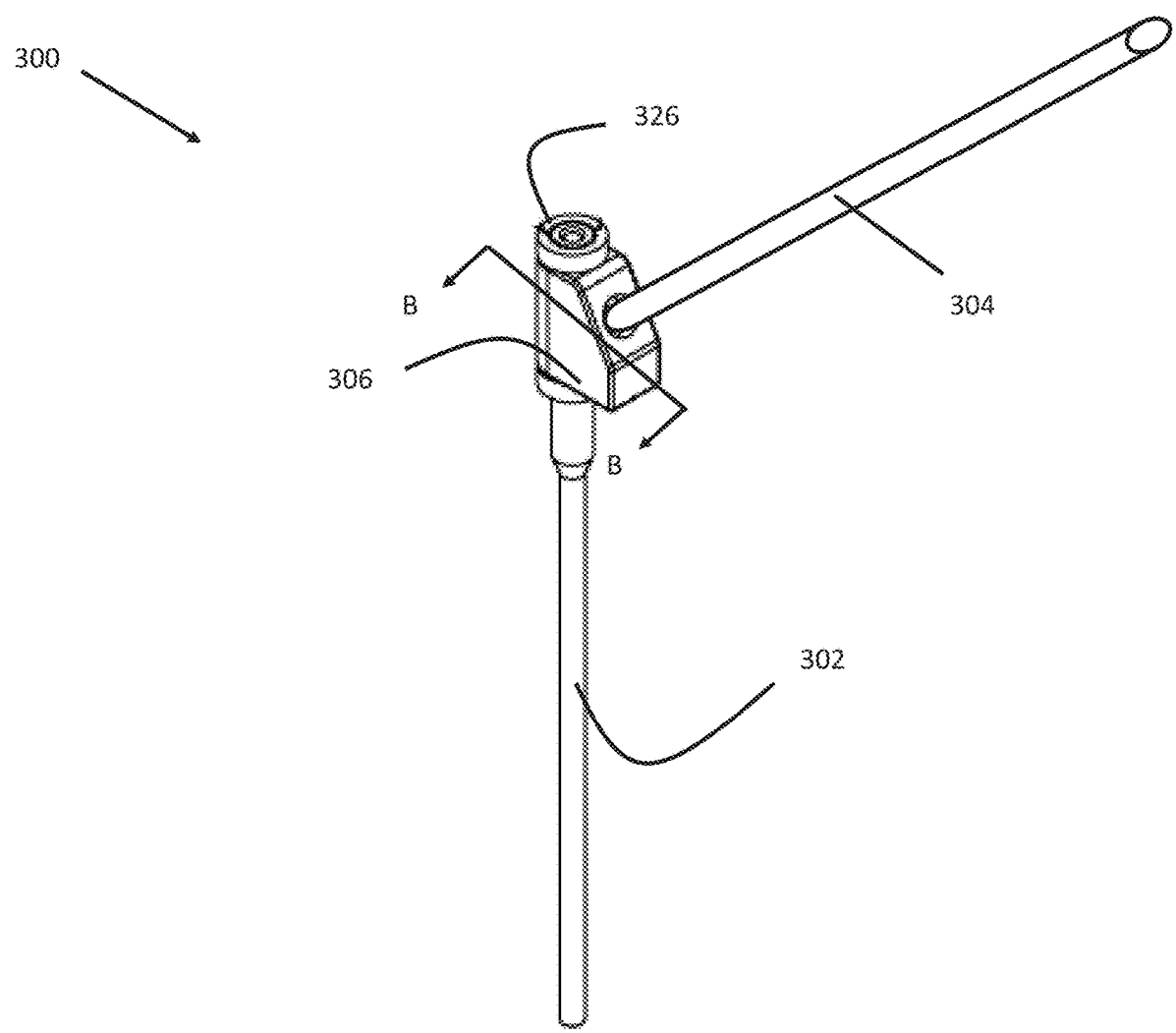
FIG. 19A illustrates an embodiment of an angled handle.
Figures 19B, 19C:
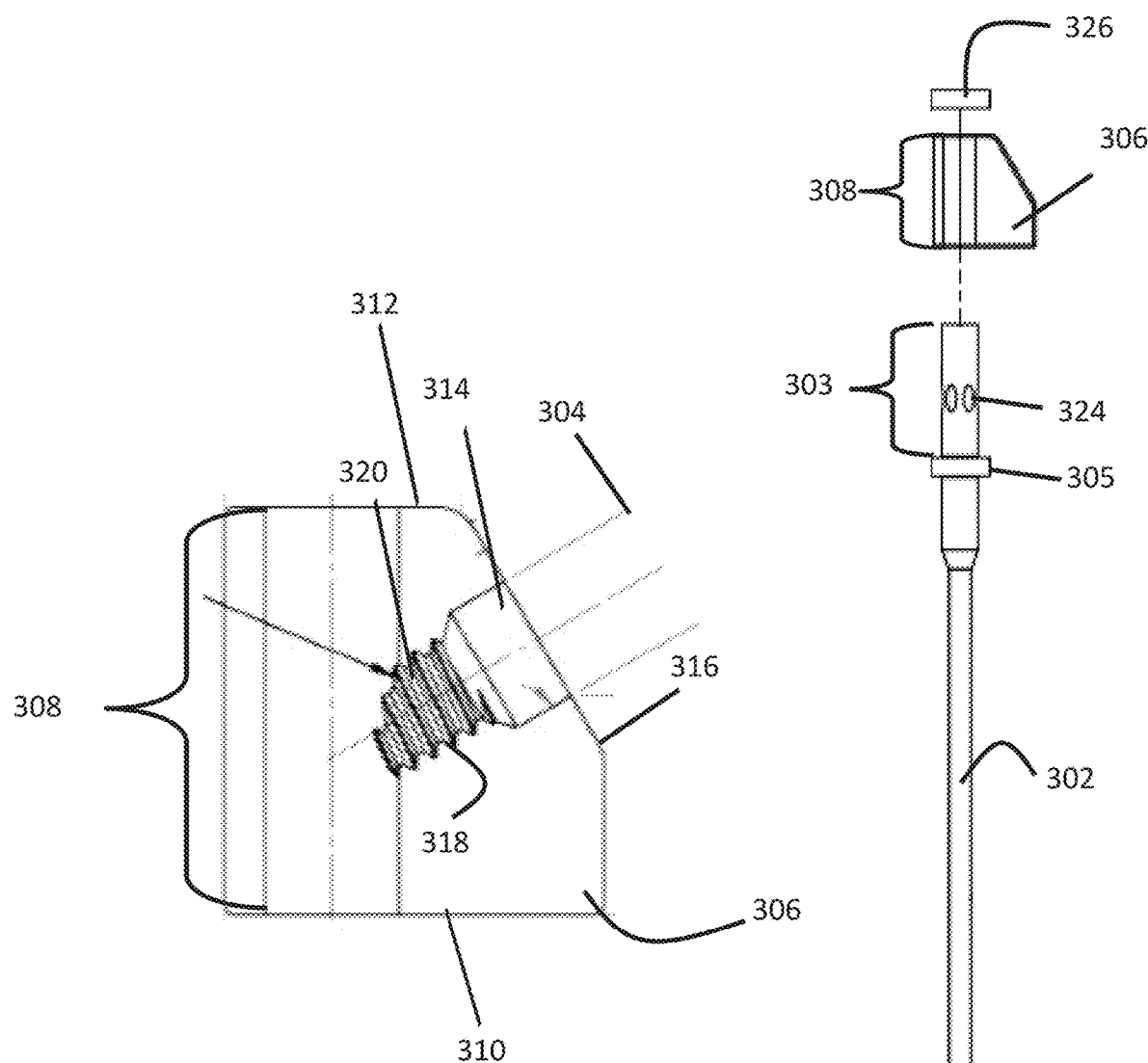
FIG. 19B illustrates a cross-sectional view of the body of an angled handle taken along line B-B in FIG. 19A.
FIG. 19C illustrates an exploded view of an embodiment of a handle.

Trial sizer 100 includes trial body 102 extending from first end 104 to an opposite second end 106. In an embodiment, trial body 102 may be hollow or partially hollow and configured to receive an instrument within trial body 102. In such cases, an instrument may be, for example, handle 200 (see FIG. 17) or other instruments for manipulating trial body 102 during a surgical operation, such as angled handle 300 (see FIG. 19). Trial body 100 includes vertebrae spacer 108 coupled to first end 104 of trial body 102 and sized to be received within the space between a first and a second adjacent vertebral body (hereinafter "intervertebral space"). Placement of spacer 108 within the intervertebral space prevents the lateral, horizontal, and vertical movements of trial sizer 100. By preventing such movement, the correct alignment of trial sizer 100 in relation to bone 41 may be achieved.

Trial sizer 100 is prevented from being disposed within the intervertebral space at a depth that may cause injury to the patient's spine by flange 114. In an embodiment, one or more flanges 114 may protrude from spacer 108. Upon placement of spacer 108 into the intervertebral space, at least a portion of flange 114 contacts at least a portion of one or both of the vertebral bodies. The contacting of flange 114 with one or more of the vertebral bodies provides a tactile and/or visual indication that trial sizer 100 is positioned at the prescribed depth within the intervertebral space.

Spacer 108 is ideally formed having a rectangular prism shape, however, spacer 108 may include various geometries and sizes depending on an individual patient's spinal anatomy. For example, larger patients may require a thicker spacer 108 than patients with more petite body builds, such as younger patients. When the need arises for a different spacer 108, spacer 108 may be simply uncoupled from first end 104 of trial body 102 and replaced with spacer 108 of an appropriate size. This swapping of spacer 108 allows the surgeon and medical staff to tailor the placement of trial body 100 based on each individual patient's anatomy, ensuring optimal placement of the pilot holes. In such embodiments, spacer 108 may be coupled to trial body 102 by threads, magnetic attraction, or any other method known to a person of ordinary skill in the art that would allow for quick and easy swapping of spacer 108 during surgery.

Upon proper alignment of trial sizer 100, the surgeon may then use pilot hole guides 116 to align the surgical drill and subsequently drill the pilot hole at the correct angle within bone 41. Each of the pilot hole guides 116A and 116B extend from a first end 118 to a second end 120 and may be coupled to trial body 102 in various geometric configurations and angles. For example, pilot hole guides 116A and 116B may be angled at angle β and arranged in an isosceles triangle configuration, shown best in FIG. 16A. However, the configuration of pilot hole guides 116A and 116B are complementary to the orientation of apertures 71 of plate 80. For example, pilot hole guides 116 may be in substantially the same orientation and angle as apertures 71, such that when the pilot hole is drill, fasteners 70 are positioned at the correct orientation thereby ensuring that fasteners 70 properly align with and thereby engage apertures 71 of plate 80 when fasteners are disposed through the surface of bone 41.

Generally, pilot hole guides 116A and 116B are tubular in shape but may be any shape, that allows for the drill bit to pass through pilot hole guides 116. Further, in an embodiment, second end 120 of pilot hole guide 116 may include cutaway portion 122 for viewing of the drilling field as the drill bit passes through pilot hole guide 116 and engages with bone 41 when drilling out the pilot hole.

In an embodiment, second end 120 of pilot hole guide 116 extends away from first end 118 at a predetermined distance, which in some embodiments may determine the depth at which drill bit may be inserted into bone 41. For example, when drill bit drills into bone 41 at a prescribed depth, the drill may make contact with the first end 118 of pilot hole guide 116 preventing the drill bit from progressing deeper into bone 41. In an embodiment, the drill bit may include a visual indicator, such as a painted line as a visual representation of the depth viewable through the cutaway portion.

The prescribed depth at which the pilot hole is required to be drilled may be determined based on x-ray and/or magnetic resonance machine (MRI) imaging prior to or during surgery.

FIGS. 18A-18C depict handle 200 used to position plate 80 and/or trial guide 100. Handle 100 includes elongated body 202 extending from first end 204 to second end 206. Outer surface 208 of body 202 may be formed having ridges, bumps, slots, or other features designed to increase the grippability of body 202 in both wet and dry conditions. Disposed at an end of shaft 212 and positioned most distal from body 202 is engagement portion 214 having engagement threads 216 configured to threadedly engage trial body 102 of trial sizer 100 or engagement apertures 78 of plate 80.

In an embodiment, handle 202 is formed having internal channel 210 extending at least partially from first end 204 to second end 206 and configured to receive shaft 212. Shaft 212 is disposed within internal channel 210 and secured within internal channel 210 using magnetic attraction, press-fitting, or other methods know in the art to secure shaft 212 within internal channel 210. In an embodiment, shaft 212 and body 202 may be a single unit formed by, for example, injection molding.

FIGS. 19A-19E depict angled handle 300, which provides greater control and manipulation of plate 80 and/or trial sizer 100. Angled handle 300 includes first member 302 and second member 304 removably coupled to body 306. First member 302 and second member 304 are positioned at an angle with respect to one another. In an embodiment, the angle may be a right angle, an obtuse angle, or any angle between 0 degrees and 180 degrees. Body 306 includes first member channel 308 disposed between first side 310 and second side 312. Second member channel 314 is disposed between third side 316 and first member channel 308, such that first member channel 308 and second member channel 314 may be in communication with one another. Second member channel 314 includes thread receipt 318 and is configured to receive threads 320 of second member 304.

First member 302 includes handle flange 305 and is configured to be slidably disposed within first member channel 308 until handle flange 305 abuts first side 310 of body 306, indicating that first member 302 is fully disposed within first member channel 308. When handle flange 305 contacts first side 310, a portion of first member 302 protrudes from second side 312 of body 306. Retention ring 326 may then be disposed circumferentially around first portion 303 of first member 302 and prevents first member 302 from being removed from first member channel 308 accidentally. In such a configuration at least first portion 303 of first member 302 is disposed within member channel 308. In an embodiment, first portion 303 includes a plurality of indents 324 configured to receive a portion of second member 304.

Second member 304 includes threads 320 and is configured to threadably couple with thread receipt 318 of second member channel 314, thereby securing second member 304 within second member channel 314. When second member 304 is secured within second member channel 314, at least a portion of second member 304 is received within at least one of the plurality of indents 324 of first portion 303 of first member 302. Thus, when second member 304 is secured within second member channel 314, the axial rotation of first member 302 about a center longitudinal axis with respect to body 306 is hindered.

Figure 20:
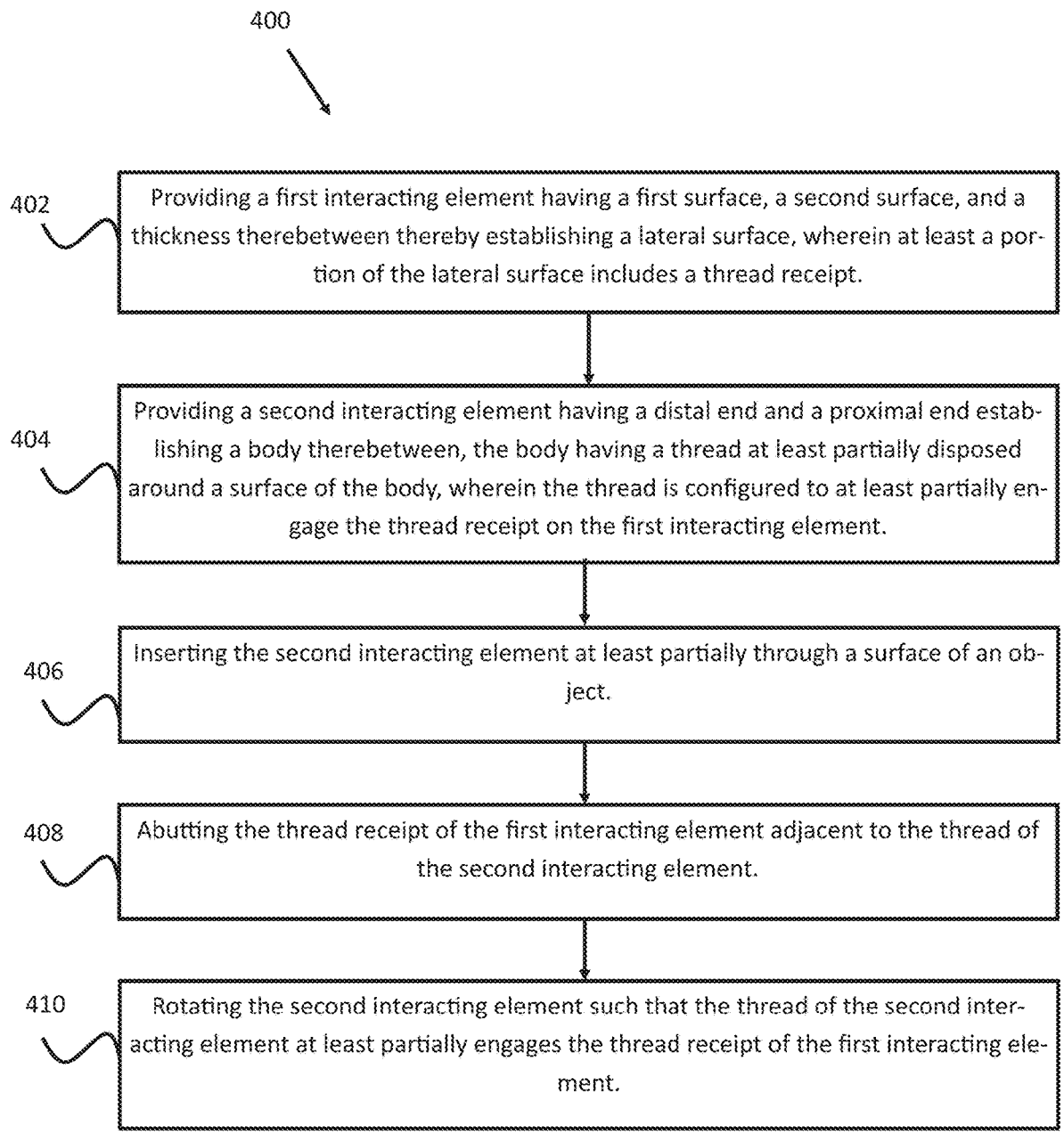
FIG. 20 is a flow chart diagram for a method for the method of securing a first interacting element to a second interacting element.

FIG. 20, in conjunction with FIGS. 1-19E, provides a flowchart of an embodiment of the method 400 of securing a first interacting element to a second interacting element.

The steps delineated in the exemplary process flowchart of FIG. 20 are merely exemplary of a preferred order for the method of securing a first interacting element to a second interacting element. In an embodiment, the steps may be carried out in another order, with or without additional steps included therein. Additionally, the steps may be carried out with an alternative embodiment of the apparatus disclosed above.

The method 400 for securing a first interacting element to a second interacting element begins at step 402 in which a first interacting element is provided. The first interacting element has a first surface and a second surface and a thickness therebetween, thereby establishing a lateral surface. At least a portion of the lateral surface includes a thread receipt. At step 404, a second interacting element is provided having a distal end and a proximal end establishing a body therebetween. The body has a thread at least partially disposed around a surface of the body. The thread is configured to at least partially engage the thread receipt on the first interacting element.

At step 406, the second interacting element is partially inserted through a surface of an object. Next, the thread receipt of the first interacting element is positioned adjacent to the thread of the second interacting element as depicted in step 408. Then, in step 410, the second interacting element is rotated such that the thread of the second interacting element is at least partially received in the thread receipt of the first interacting element. The second interacting element can be further tightened to secure the first interacting element in place. Then, the remaining holes can be drilled and/or the remaining fasteners can be threaded into the object in locations to ensure that the threads on the first interacting elements threadedly engage the thread receipts in the remaining open apertures in the first interacting element.

Figure 21:
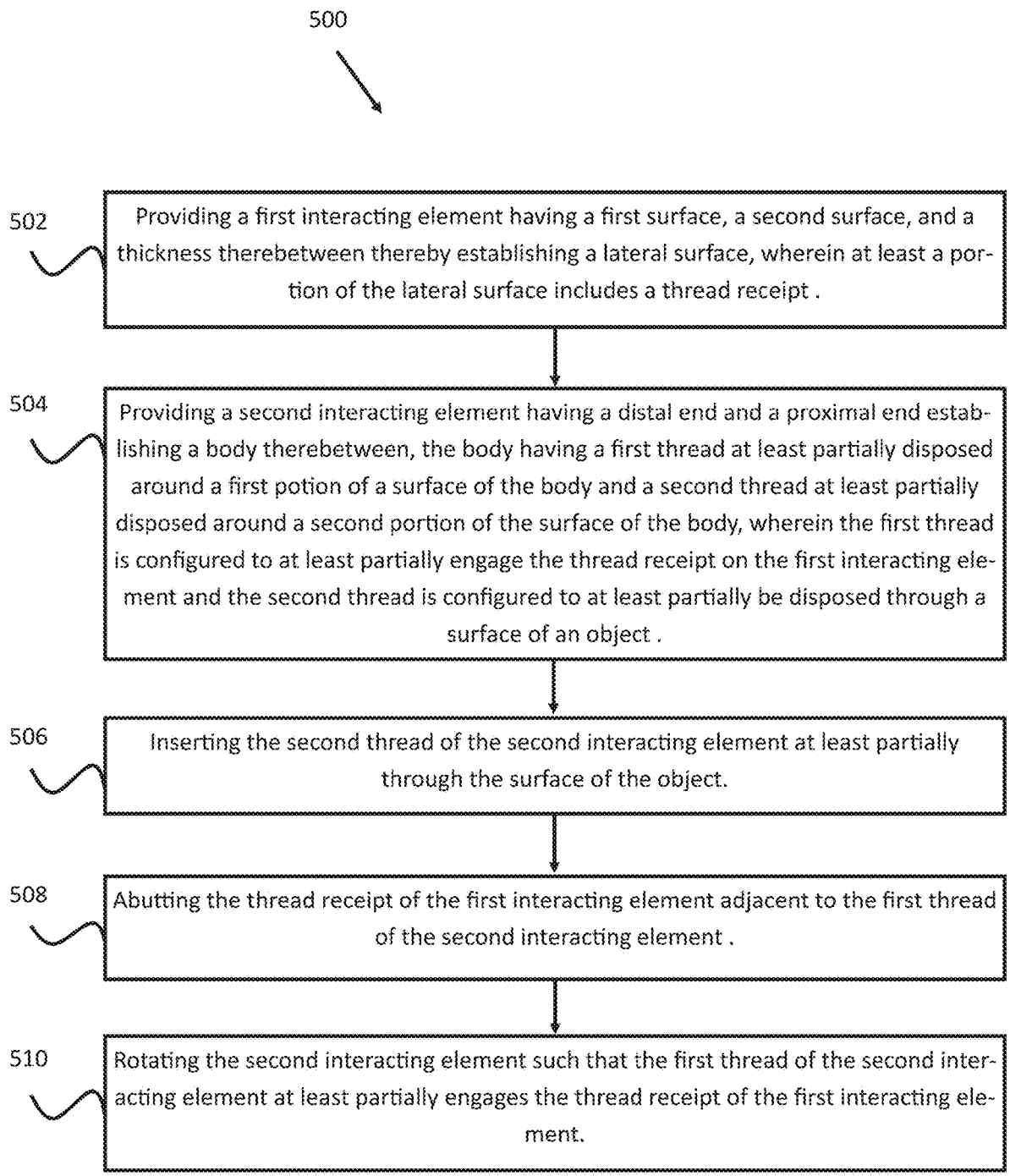
FIG. 21 is a flow chart diagram for an embodiment of the method of securing a first interacting element to a second interacting element

FIG. 21, another embodiment of the method of securing a first interacting element to a second interacting element. The method 500 for the securing a first interacting element to a second interacting element begins at step 502 in which a first interacting element has a first surface, a second surface, and a thickness therebetween thereby establishing a lateral surface. At least a portion of the lateral surface includes a thread receipt. In step 504, a second interacting element having a distal end and a proximal end establishing a body therebetween is provided. The body has a first thread at least partially disposed around a first portion of a surface of the body and a second thread at least partially disposed around a second portion of the surface of the body. The first thread is configured to at least partially engage the thread receipt on the first interacting element and the second thread is configured to at least partially be disposed through a surface of an object. In step 506, the second thread is partially inserted through the surface of the object. Next, in step 508, the thread receipt of the first interacting element positioned adjacent to the first thread of the second interacting element. Finally, in step 510, the second interacting element is rotated such that the first thread of the second interacting element is at least partially engaged with the thread receipt of the first interacting element. The second interacting element can be further tightened to secure the first interacting element in place. Then, the remaining holes can be drilled and/or the remaining fasteners can be threaded into the object in locations to ensure that the threads on the first interacting elements threadedly engage the thread receipts in the remaining open apertures in the first interacting element.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of securing a first interacting element to a second interacting element, the method comprising the steps of:
    providing a first interacting element having a first surface, a second surface, and a thickness therebetween, thereby establishing a lateral surface, wherein at least a portion of the lateral surface includes a thread receipt within a semicircular opening;
    providing a second interacting element having a distal end and a proximal end establishing a body therebetween, the body having a thread at least partially disposed around a surface of the body, wherein the thread is configured to at least partially engage the thread receipt on the first interacting element;
    threading the second interacting element partially through a surface of an object;
    abutting the thread receipt of the first interacting element adjacent to the thread of the second interacting element, wherein the step of initially threading the second interacting element occurs prior to abutting the thread receipt of the second interacting element adjacent to the thread of the second interacting element; and
    rotating the second interacting element such that the thread of the second interacting element at least partially engages the thread receipt of the first interacting element.

2. The method of claim 1, wherein the first interacting element further includes a body portion and a pair of fastening cantilevers positioned on opposite sides of the body portion and bent out of a plane at a first angle, the plane residing parallel to the first and the second surfaces of the first interacting element.

3. The method of claim 2, further including a step of inserting the second interacting element at a second angle that matches the first angle of the pair of fastening cantilevers.

4. The method of claim 2, further including a step of inserting the second interacting element at a second angle between 5 degrees and 30 degrees.

5. The method of claim 1, further including a step of inserting the second interacting element further within the surface of the object, such that the engagement between the thread of the second interacting element and the thread receipt of the first interacting element locks the first interacting element in place.

6. The method of claim 1, further comprising rotating the second interacting element until an end cap positioned at the proximal end of the body abuts the first interacting element.

7. The method of claim 1, further comprising drilling a pilot hole, wherein the pilot hole is configured to guide the second interacting element into the object when the second interacting element is inserted through the surface of the object.

8. The method of claim 1, wherein the first interacting element further includes an engagement aperture at least partially disposed through the first surface, the engagement aperture including an internal thread receipt.

9. The method of claim 8, further comprising coupling a handle to the first interacting element, wherein the handle includes a handle thread configured to be received by the engagement aperture of the first interacting element, thereby increasing control over the first interacting element.

10. The method of claim 1, wherein the thread receipt of the first interacting element resides within a semi-circular aperture forming the portion of the lateral surface.

11. The method of claim 10, wherein the step of abutting the thread receipt of the first interacting element adjacent to the thread of the second interacting element includes partially encircling the second interacting element within the semi-circular aperture forming the portion of the lateral surface of the first interacting element.

12. The method of claim 1, wherein the thread includes a thread base surface and an outer thread surface, the outer thread surface being smaller in length near a thread termination end and larger in length near a thread origination end, such that the thread is configured to permit locking of the thread within the thread receipt.

13. The method of claim 1, wherein the second interacting element includes a cutting flute.

14. A method of securing a cervical plate to a fastener, the method comprising the steps of:
providing the cervical plate having a first surface, a second surface, and a thickness therebetween thereby establishing a lateral surface, wherein at least a portion of the lateral surface includes a thread receipt;
providing the fastener having a distal end and a proximal end establishing a body and longitudinal axis therebetween, the body having a thread at least partially disposed around a surface of the body, wherein the thread is configured to at least partially engage the thread receipt on the cervical plate;
initially inserting the fastener partially through a surface of a bone independently from the cervical plate;
transversely translating the cervical plate relative to the longitudinal axis of the fastener to bring the thread receipt of the cervical plate into abutting relation with the thread of the fastener, wherein the step of initially inserting the fastener occurs prior to abutting the thread receipt of the cervical plate adjacent to the thread of the fastener; and
rotating the fastener such that the thread of the fastener at least partially engages the thread receipt of the cervical plate.

15. The method of claim 14, wherein the cervical plate further includes a body portion and a pair of fastening cantilevers positioned on opposite sides of the body portion and bent out of a plane at a first angle, the plane residing parallel to the first and the second surfaces of the first interacting element.

16. The method of claim 15, further including the step of inserting the fastener at a second angle that matches the first angle of the pair of fastening cantilevers.

17. The method of claim 15, further including the step of inserting the fastener at a second angle between 5 degrees and 30 degrees.

18. The method of claim 14, further including the step of inserting the fastener further within the surface of the bone, such that the engagement between the thread of the fastener and the thread receipt of the cervical plate locks the first interacting element in place.

19. A method of securing a first interacting element to a second interacting element, the method comprising the steps of:
providing a first interacting element having a first surface, a second surface, and a thickness therebetween thereby establishing a lateral surface, wherein at least a portion of the lateral surface is semi-circular and includes a thread receipt;
providing a second interacting element having a distal end and a proximal end establishing a body and longitudinal axis therebetween, the body having a first thread at least partially disposed around a first portion of a surface of the body and a second thread partially disposed around a second portion of the surface of the body, wherein the first thread is configured to at least partially engage the thread receipt on the first interacting element and the second thread is configured to at least partially be disposed through a surface of an object;
rotatably inserting the second thread of the second interacting element at least partially through the surface of the object, wherein the second interacting element is partially inserted through the surface of the object separately from the first interacting element;
transversely translating the first interacting element relative to the longitudinal axis of the second interacting element to bring the thread receipt of the first interacting element into abutting relation with the first thread of the second interacting element, wherein the step of rotatably inserting the second interacting element occurs prior to transversely translating the first interacting element to bring the thread receipt of the first interacting element into abutting relation with the thread of the second interacting element; and
rotating the second interacting element such that the first thread of the second interacting element at least partially engages the thread receipt of the first interacting element.

20. The method of claim 19, wherein the first interacting element further includes a body portion and a pair of fastening cantilevers, the pair of fastening cantilevers are bent out of a plane at an angle between 5 degrees and 30 degrees.

* * * * *